United States Patent
Green et al.

(10) Patent No.: US 12,234,254 B2
(45) Date of Patent: Feb. 25, 2025

(54) METHODS FOR PRODUCING CRYSTALLINE L-GLUFOSINATE AMMONIUM MONOHYDRATE

(71) Applicant: BASF SE, Ludwigshafen (DE)

(72) Inventors: Brian Michael Green, Lutherville, MD (US); Rachel Melissa Witek, New Market, MD (US); Nadejda Pavlova, Gaithersburg, MD (US); Matthew Richard Oberholzer, Wilmington, DE (US)

(73) Assignee: BASF SE, Ludwigshafen (DE)

( * ) Notice: Subject to any disclaimer, the term of this patent is extended or adjusted under 35 U.S.C. 154(b) by 681 days.

(21) Appl. No.: 17/603,759

(22) PCT Filed: Apr. 15, 2020

(86) PCT No.: PCT/US2020/028191
§ 371 (c)(1),
(2) Date: Oct. 14, 2021

(87) PCT Pub. No.: WO2020/214631
PCT Pub. Date: Oct. 22, 2020

(65) Prior Publication Data
US 2022/0177499 A1  Jun. 9, 2022

Related U.S. Application Data

(60) Provisional application No. 62/978,005, filed on Feb. 18, 2020, provisional application No. 62/834,675, filed on Apr. 16, 2019.

(51) Int. Cl.
*C07F 9/30* (2006.01)
*C12N 9/06* (2006.01)

(52) U.S. Cl.
CPC ............ *C07F 9/301* (2013.01); *C12N 9/0024* (2013.01); *C12Y 104/03003* (2013.01); *C07B 2200/13* (2013.01)

(58) Field of Classification Search
CPC ... C07B 2200/13; C07F 9/301; C12N 9/0024; C12Y 104/03003
See application file for complete search history.

(56) References Cited

U.S. PATENT DOCUMENTS

| | | | |
|---|---|---|---|
| 4,499,027 A | 2/1985 | Minowa et al. | |
| 4,647,692 A | 3/1987 | Jacewicz | |
| 5,420,329 A | 5/1995 | Zeiss | |
| 5,767,309 A | 6/1998 | Knorr et al. | |
| 5,869,668 A | 2/1999 | Knorr et al. | |
| 7,772,426 B2 | 8/2010 | Minowa et al. | |
| 7,795,464 B2 | 9/2010 | Minowa et al. | |
| 8,076,503 B2 | 12/2011 | Minowa et al. | |
| 9,834,802 B2 | 12/2017 | Green et al. | |
| 10,260,078 B2 | 4/2019 | Green et al. | |

FOREIGN PATENT DOCUMENTS

| | | | |
|---|---|---|---|
| CN | 106188134 | * | 7/2016 |
| CN | 106188134 A | | 12/2016 |
| WO | WO-2018/108797 A1 | | 6/2018 |
| WO | WO2019/018406 | * | 1/2019 |
| WO | WO-2019/018406 A1 | | 1/2019 |
| WO | WO-2020/214631 A1 | | 10/2020 |

OTHER PUBLICATIONS

CN106188134 translated (Year: 2016).*
U.S. Appl. No. 16/631,963, Nonfinal Office Action, dated May 25, 2022.
European Patent Application No. 20724290.0, Applicant's counter-argument after entry into European phase, submitted with the European Patent Office on May 18, 2022.
Miller et al., Chapter 3: Solvent systems for crystallization and polymorph selection, pp. 53-109, IN: Augustijns et al. (eds.), Solvent Systems and Their Selection in Pharmaceutics and Biopharmaceutics, Springer (2007).
Bartsch et al., Stereospecific production of the herbicide phosphinothricin (glufosinate): purification of aspartate transaminase from *Bacillus stearothermophilus*, cloning of the corresponding gene, aspC, and application in a coupled transaminase process, Appl. Environ. Microbiol., 62(10):3794-9 (1996).
International Application No. PCT/US2020/028191, International Search Report and Written Opinion, mailed Jul. 9, 2020.
Pollegioni et al., New biotech applications from evolved D-amino acid oxidases, Trends Biotechnol., 29(6):276-83 (2011).

* cited by examiner

*Primary Examiner* — Yevgeny Valenrod
*Assistant Examiner* — Blaine G Doletski
(74) *Attorney, Agent, or Firm* — MARSHALL, GERSTEIN & BORUN LLP

(57) ABSTRACT

Methods for preparing crystalline L-glufosinate ammonium monohydrate are disclosed. The methods include forming a mixture comprising water, a water-miscible organic solvent, ammonium hydroxide, and a glufosinate starting material containing L-glufosinate ammonium and D-glufosinate ammonium. L-Glufosinate ammonium monohydrate is crystallized and separated from the mixture, providing L-glufosinate ammonium monohydrate Form B. Compositions and methods employing the crystalline L-glufosinate ammonium monohydrate are also described.

35 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 368
<212> TYPE: PRT
<213> ORGANISM: Rhodosporidium toruloides

<400> SEQUENCE: 1

Met His Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Asn Trp Thr Pro Phe Met Thr Leu Thr Asp Gly
    50                  55                  60

Pro Arg Gln Ala Lys Trp Glu Glu Ser Thr Phe Lys Lys Trp Val Glu
65                  70                  75                  80
```

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Gly Ala Ile
            115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
            245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 2
<211> LENGTH: 375
<212> TYPE: PRT
<213> ORGANISM: Rhodosporidium toruloides

<400> SEQUENCE: 2

Met Ala Ser Pro Ser Asn Lys Gln Ile Val Val Leu Gly Ala Gly Val
1               5                   10                  15

Ile Gly Leu Thr Thr Ala Val Lys Ile Gln Glu Gln Arg Gly Tyr Gln
            20                  25                  30

Val Thr Ile Ile Ala Glu Ile Leu Pro Ser Asp Pro Lys Ser Ile Arg
        35                  40                  45

Tyr Thr Ser His Trp Ala Gly Ala His His Val Ser Leu Ala Gly Glu
    50                  55                  60

Asp Lys Leu Gln Ala Arg Val Asp Gln Glu Thr Phe Gly Val Met Trp
65                  70                  75                  80

Glu Met Ser Ala Pro Gly Gly Glu Ala Glu Gly Cys Phe Leu Arg Gln
                85                  90                  95

Lys Gln Val Glu Tyr Tyr Cys Asp Lys Gln Ala Asp Pro His Pro Leu
            100                 105                 110

Glu His Met Pro Asp Phe Arg Arg Leu Asp Glu Asn Ser Leu Ile Pro
            115                 120                 125

Asn Thr Val Ala Gly Ile Gly Phe Thr Thr Leu Thr Ile Asp Thr Pro
130                 135                 140

Ile Tyr Leu Asn Tyr Leu Leu Ser Arg Phe Leu Ala Arg Gly Gly Ala
145                 150                 155                 160

Ile Val Arg Gly Ser Val Gln His Ile Ser Gln Val Val Asp Gly Gly
                165                 170                 175

Ala Arg Val Phe Thr Gly Ser Lys Ser Ala Gly Val Pro Val Asp Ala
                180                 185                 190

Val Ile Val Cys Ala Gly Ile Gly Ala Arg Phe Leu Gly Gly Val Glu
            195                 200                 205

Asp Lys Asp Val Tyr Pro Ile Arg Gly Gln Thr Val Leu Leu Arg Ala
            210                 215                 220

Pro Trp Ile Arg Phe Gly Arg Thr Met Ser Ser Lys Asp Gly Leu Tyr
225                 230                 235                 240

Thr Tyr Ile Ile Pro Arg Arg Ser Gly Asp Val Ile Val Gly Gly Ile
                245                 250                 255

Lys Val Pro Asn Asp Trp Tyr Pro Thr Pro Arg Pro Glu Thr Thr Gln
            260                 265                 270

Asp Ile Leu Lys Arg Gly Leu Ala Leu Cys Pro Glu Leu Ala Pro Gln
            275                 280                 285

Ser Ile Arg Asp Gln Arg Glu Pro Thr Val Asp Asp Leu Arg Pro Leu
            290                 295                 300

Val Ile Glu Glu Gly Cys Gly Leu Arg Pro Gly Arg Lys Gly Gly Ile
305                 310                 315                 320

Arg Leu Glu Val Glu Trp Tyr Ala Lys Thr Asp Gly Gln Ala Pro Lys
                325                 330                 335

Val Pro Ile Val His Asn Tyr Gly His Gly Gly Ala Gly Phe Gln Ala
            340                 345                 350

Ser Trp Gly Ser Ala Ser Val Ala Leu Glu Leu Leu Glu Lys Ala Leu
            355                 360                 365

Ala Gln Ala Arg Leu Ala Met
            370                 375

<210> SEQ ID NO 3
<211> LENGTH: 368
<212> TYPE: PRT
<213> ORGANISM: Rhodosporidium toruloides

<400> SEQUENCE: 3

Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Asn Pro His Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe

```
                85                  90                  95
Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 4
<211> LENGTH: 27
<212> TYPE: PRT
<213> ORGANISM: Rhodosporidium toruloides

<400> SEQUENCE: 4

Met Gly Ser Ser His His His His His His Ser Ser Gly Leu Val Pro
1               5                   10                  15

Arg Gly Ser His Met Met Ala Arg Ile Arg Leu
            20                  25

<210> SEQ ID NO 5
<211> LENGTH: 395
<212> TYPE: PRT
<213> ORGANISM: Rhodosporidium toruloides

<400> SEQUENCE: 5

Met Gly Ser Ser His His His His His His Ser Ser Gly Leu Val Pro
1               5                   10                  15

Arg Gly Ser His Met Met Ala Arg Ile Arg Leu Met His Ser Gln Lys
```

```
            20                  25                  30
Arg Val Val Val Leu Gly Ser Gly Val Ile Gly Leu Ser Ser Ala Leu
                35                  40                  45
Ile Leu Ala Arg Lys Gly Tyr Ser Val His Ile Leu Ala Arg Asp Leu
 50                  55                  60
Pro Glu Asp Val Ser Ser Gln Thr Phe Ala Ser Pro Trp Ala Gly Ala
 65                  70                  75                  80
Val Trp Asn Pro His Met Thr Leu Thr Asp Gly Pro Arg Gln Ala Lys
                85                  90                  95
Trp Glu Glu Ser Thr Phe Lys Lys Trp Val Glu Leu Val Pro Thr Gly
                100                 105                 110
His Ala Met Trp Leu Lys Gly Thr Arg Arg Phe Ala Gln Asn Glu Asp
                115                 120                 125
Gly Leu Leu Gly His Trp Tyr Lys Asp Ile Thr Pro Asn Tyr Arg Pro
 130                 135                 140
Leu Pro Ser Ser Glu Cys Pro Gly Ala Ile Gly Val Thr Tyr Asp
 145                 150                 155                 160
Thr Leu Ser Val His Ala Pro Lys Tyr Cys Gln Tyr Leu Ala Arg Glu
                165                 170                 175
Leu Gln Lys Leu Gly Ala Thr Phe Glu Arg Arg Thr Val Thr Ser Leu
                180                 185                 190
Glu Gln Ala Phe Asp Gly Ala Asp Leu Val Val Asn Ala Thr Gly Leu
                195                 200                 205
Gly Ala Lys Ser Ile Ala Gly Ile Asp Asp Gln Ala Ala Glu Pro Ile
 210                 215                 220
Arg Gly Gln Thr Val Leu Val Lys Ser Pro Cys Lys Arg Cys Thr Ser
 225                 230                 235                 240
Asp Ser Ser Asp Pro Ala Ser Pro Ala Tyr Ile Ile Pro Arg Pro Gly
                245                 250                 255
Gly Glu Val Ile Cys Gly Gly Thr Tyr Gly Val Gly Asp Trp Asp Leu
                260                 265                 270
Ser Val Asn Pro Glu Thr Val Gln Arg Ile Leu Lys His Cys Leu Arg
                275                 280                 285
Leu Asp Pro Thr Ile Ser Ser Asp Gly Thr Ile Glu Gly Ile Glu Val
 290                 295                 300
Leu Arg His Asn Val Gly Leu Arg Pro Ala Arg Gly Gly Pro Arg
 305                 310                 315                 320
Val Glu Ala Glu Arg Ile Val Leu Pro Leu Asp Arg Thr Lys Ser Pro
                325                 330                 335
Leu Ser Leu Gly Arg Gly Ser Ala Arg Ala Ala Lys Glu Lys Glu Val
                340                 345                 350
Thr Leu Val His Ala Tyr Gly Phe Ser Ser Ala Gly Tyr Gln Gln Ser
                355                 360                 365
Trp Gly Ala Ala Glu Asp Val Ala Gln Leu Val Asp Glu Ala Phe Gln
                370                 375                 380
Arg Tyr His Gly Ala Ala Arg Glu Ser Lys Leu
 385                 390                 395
```

METHODS FOR PRODUCING CRYSTALLINE L-GLUFOSINATE AMMONIUM MONOHYDRATE

CROSS REFERENCE TO RELATED APPLICATIONS

This application is the U.S. national phase of International Application No. PCT/US2020/028191, filed Apr. 15, 2020, which claims priority to U.S. Provisional Application No. 62/834,675, filed Apr. 16, 2019, and U.S. Provisional Application No. 62/978,005, filed Feb. 18, 2020, which are incorporated herein by reference in their entireties.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named "M202650A Seglisting.txt" which was created on Oct. 5, 2021, and having a size of 13,756 bytes and is filed concurrently with the specification. The sequence listing contained in this ASCII formatted document is part of the specification and is herein incorporated by reference in its entirety.

BACKGROUND OF THE INVENTION

The biological activities of the individual molecules of a racemic substance usually differ and often only one, of the two enantiomers, exhibits significant activity. Such is the case with D, L-glufosinate, which is a non-selective, foliarly-applied herbicide used worldwide in high volume. L-glufosinate inhibits the glutamine synthetase enzyme in plants which leads to plant death but the D-glufosinate enantiomer has essentially no herbicidal activity (Ruhland et al. (2002) *Environ. Biosafety Res.* 1:29-37). Nearly all of the current commercial glufosinate production is racemate (Duke et al. 2010 *Toxins* 2:1943-1962), which means that only about half of what is applied to agricultural land is useful; the other half represents a load on the environment without any benefit.

L-glufosinate can be produced by asymmetric chemical synthesis as disclosed in U.S. Pat. Nos. 4,499,027, 5,420,329, 7,772,426, 7,795,464, and 8,076,503. While these methods are technically feasible, none has proven cost-effective commercially compared to the production of racemic glufosinate. Resolution of racemates can be achieved in many instances by forming a diastereomer or a diastereomeric salt with another chiral compound; examples of this technique used with alpha amino acids are disclosed in U.S. Pat. No. 4,647,692. The technique can be used with quinine or cinchonine to resolve racemic glufosinate as disclosed by U.S. Pat. Nos. 5,767,309 and 5,869,668. WO 2018/108797 discloses the resolution of racemic glufosinate using (-)-ephedrine. However, ephedrine is subject to increasing regulation and control by most government agencies worldwide to prevent diversion for the illicit production of methamphetamine. Other methods have been disclosed in which the inactive D-glufosinate in racemic glufosinate is converted to the active L-glufosinate, as described in U.S. Pat. No. 9,834,802 and WO 2019/018406. L-glufosinate produced in a stable solid form is highly desirable for commercial manufacture. Therefore, methods to exclusively produce the L-glufosinate enantiomer are desirable.

BRIEF SUMMARY OF THE INVENTION

Compositions and methods for the preparation and use of crystalline L-glufosinate ammonium monohydrate are provided. In one aspect, the present disclosure provides a method for preparing crystalline L-glufosinate ammonium monohydrate. The method includes:

(i) forming a mixture comprising a glufosinate starting material and an aqueous solution,
   wherein the glufosinate starting material comprises L-glufosinate ammonium and D-glufosinate ammonium, and
   wherein the aqueous solution comprises water, a water-miscible organic solvent, and optionally a source of ammonia such as ammonium hydroxide;
(ii) crystallizing L-glufosinate ammonium monohydrate from the mixture of step (i) to form L-glufosinate ammonium monohydrate crystals; and
(iii) separating at least a portion of the L-glufosinate ammonium monohydrate crystals from the aqueous solution following step (ii);
thereby preparing the crystalline L-glufosinate ammonium monohydrate;
wherein the crystalline L-glufosinate ammonium monohydrate comprises L-glufosinate ammonium monohydrate Form B.

In some embodiments, L-glufosinate seed crystals are used in step (ii), the crystallizing step.

Methods for desalting and for the final isolation of crystalline L-glufosinate ammonium monohydrate are further described herein. The methods for obtaining crystalline forms of L-glufosinate can include obtaining crystalline L-glufosinate from any racemic mixture of glufosinate. As such, the methods described herein can also be used to further obtain crystalline L-glufosinate after enzymatic conversion of D-glufosinate to L-glufosinate. Upon generation of a mixture containing L-glufosinate as described in U.S. Pat. Nos. 9,834,802; 10,260,078; and PCT/US2018/042503 (herein incorporated by reference in their entireties), the solution may be subjected to the following methods for obtaining an L-glufosinate mixture enriched in L-glufosinate. Thus, any D- and L-glufosinate mixture can be subjected to the methods described herein to obtain crystalline L-glufosinate. Such methods can include the following:

Method I: Desalting. The desalting method comprises the following steps:

(i) charging to a reactor a mixture comprising glufosinate starting material and an aqueous solution and agitating the mixture;
(ii) adjusting the pH of the solution to between pH 6 and 7 using a "source of ammonia";
(iii) concentrating the resulting solution under reduced pressure in a reactor, at a jacket temperature of about 70° C., until the total dissolved solids concentration is at least 20 to 70 wt % (e.g., 30 to 60 wt %, 40 to 50 wt %, or 45 to 50 wt %);
(iv) cooling the mixture to 2 to 15° C. and separating ammonium sulfate crystals using filtration or centrifugation, followed by adding methanol to the remaining solution to facilitate formation of additional ammonium sulfate crystals which are separated using, for example, filtration or centrifugation;
(v) drying the filtrate or supernatant solution obtained after filtration or centrifugation, respectively, using a stream of air or gas at ambient pressure or under reduced pressure at ambient or elevated temperatures to yield the "L-glufosinate starting material" (utilized in the method below). Any suitable "source of ammonia" can be used, including, for example, gaseous ammonia, ammonium hydroxide, ammonium carbonate, etc.

Method IIa: Final isolation. In one aspect, the final isolation method can include the following steps:
(i) forming a mixture comprising an "L-glufosinate starting material" (optionally obtained from the desalting method described above) and an aqueous solution,
wherein the "L-glufosinate starting material" comprises L-glufosinate ammonium and D-glufosinate ammonium, and
wherein the aqueous solution comprises water and a water-miscible organic solvent;
(ii) crystallizing L-glufosinate ammonium monohydrate from the mixture of step (i) to form L-glufosinate ammonium monohydrate crystals; and,
(iii) separating at least a portion of the L-glufosinate ammonium monohydrate crystals from the aqueous solution following step (ii);
thereby preparing the crystalline L-glufosinate ammonium monohydrate;
wherein the crystalline L-glufosinate ammonium monohydrate comprises L-glufosinate ammonium monohydrate Form B.

In some embodiments, L-glufosinate seed crystals are used in step (ii).

Method IIb: Final isolation. In another aspect, the method can include the following steps:
(i) forming a mixture comprising a "glufosinate starting material" (optionally obtained from the desalting method described above) and an aqueous solution,
wherein the "glufosinate starting material" comprises L-glufosinate ammonium and D-glufosinate ammonium, and
wherein the aqueous solution comprises water, a water-miscible organic solvent and a "source of ammonia";
(ii) crystallizing L-glufosinate ammonium monohydrate from the mixture of step (i) to form L-glufosinate ammonium monohydrate crystals; and
(iii) separating at least a portion of the L-glufosinate ammonium monohydrate crystals from the aqueous solution following step (ii);
thereby preparing the crystalline L-glufosinate ammonium monohydrate;
wherein the crystalline L-glufosinate ammonium monohydrate comprises L-glufosinate ammonium monohydrate Form B. Any suitable "source of ammonia" can be used in the method, including, but not limited to, gaseous ammonia, ammonium hydroxide and ammonium carbonate.

In some embodiments, L-glufosinate seed crystals are used in step (ii), the crystallizing step. Crystalline L-glufosinate ammonium hydrate can be formulated in compositions useful for controlling the growth of unwanted plants in agricultural fields and other areas.

DETAILED DESCRIPTION OF THE INVENTION

Figure 1:
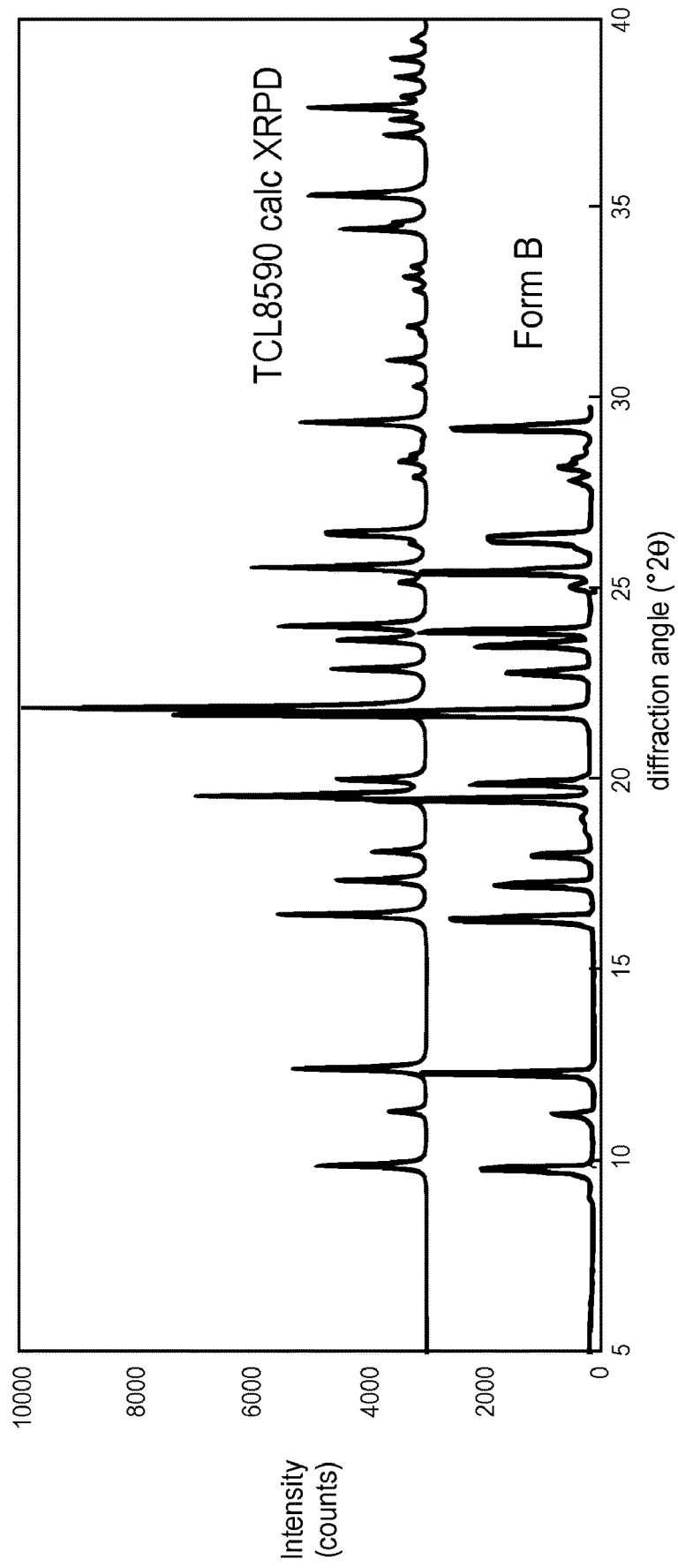
FIG. 1 shows X-ray powder diffraction (XRPD) data for L-glufosinate ammonium monohydrate Form B.

The present disclosure is based on the discovery that L-glufosinate ammonium monohydrate Form B is useful for producing purified L-glufosinate directly from a mixture containing both L-glufosinate and D-glufosinate. Consequently, L-glufosinate in ammonium form is obtained in a single step without the need to conduct a resolution step with a chiral agent or to add large amounts of acid or other unwanted substances. In some embodiments, the L-glufosinate can be obtained from the enzymatic conversion process described in U.S. Pat. Nos. 9,843,802 and 10,260,078. In that process, a D-amino acid oxidase (DAAO) and a transaminase are used to convert D-glufosinate to the L-form. The enzymes may be immobilized, for example, on to polymer beads and reused for batches.

U.S. Pat. Nos. 9,843,802 and 10,260,078 describes modified DAAO enzymes for improved enzymatic activity. Example 13, below, described additional mutant DAAO enzymes for use in the methods of the invention. The first reaction is the conversion of D-glufosinate to 4-(hydroxymethylphosphoryl)-2-oxobutanoic acid (PPO) by the DAAO enzyme.

L-glufosinate produced in a stable solid form is highly desirable for commercial manufacture. Some forms of solid L-glufosinate are hygroscopic, and therefore extra measures must be taken to eliminate contact between these solid L-glufosinate forms and water vapor. It has been observed that amorphous L-glufosinate solids are particularly hygroscopic when in contact with ambient air in the laboratory and often deliquesce. The hygroscopicity of crystalline L-glufosinate P free acid is significantly lower than that of non-crystalline L-glufosinate P free acid. Several crystalline forms of L-glufosinate are disclosed in WO 2019/018406, and two of these forms (indicated as "Form A" and "Form B") have now been identified as monohydrate crystals of L-glufosinate ammonium. Form A and Form B monohydrate crystals have low hygroscopicity compared to non-crystalline forms of L-glufosinate and are therefore more suitable for commercial manufacture.

It has been discovered that the methods used to crystallize L-glufosinate ammonium as a monohydrate crystal can result in the preferential crystallization of L-glufosinate ammonium from mixtures containing both L-glufosinate and D-glufosinate. The crystals obtained using this method, from a glufosinate starting material containing relative amounts of L-glufosinate and D-glufosinate in a ratio above the "eutectic point", have a high optical purity, that is, the crystals contain a high ratio of L-glufosinate relative to D-glufosinate. In some cases, the crystalline solids contained either no or very little D-glufosinate. The mother liquor resulting from the crystallization is enriched in D-glufosinate which can be recovered and subsequently converted to L-glufosinate by methods described herein. Crystals obtained from a glufosinate starting material below the eutectic point contain a substantial amount of both L-glufosinate and D-glufosinate and in some cases, the ratio is not very different from racemic glufosinate ammonium. Methods to produce monohydrate crystals of L-glufosinate ammonium with high optical purity and low hygroscopicity are described herein.

I. METHODS FOR SEPARATION OF SALT FROM GLUFOSINATE STARTING MATERIAL

Provided herein are methods for separating salt from glufosinate starting material (also referred to herein as desalting) in order to provide L-glufosinate starting material suitable for use in Method II as disclosed below. The salt may be selected from a group consisting of sodium sulfate, ammonium sulfate, sodium chloride, ammonium chloride, sodium citrate, ammonium citrate, sodium carbonate, ammonium carbonate, sodium bicarbonate, ammonium bicarbonate, sodium formate, ammonium formate, sodium acetate, ammonium acetate, monosodium phosphate, disodium phosphate, monoammonium phosphate, and diammonium phosphate.

Method I: Desalting. In a desalting method as described herein, a mixture comprising a glufosinate starting material and an aqueous solution is charged to a reactor and agitation is started, wherein "glufosinate starting material" comprises L-glufosinate ammonium, D-glufosinate ammonium and salt; and "aqueous solution" comprises water and a water miscible organic solvent. The pH of the solution can then be adjusted to between pH 6 and 7 using a source of ammonia, including but not limited to gaseous ammonia, ammonium hydroxide or ammonium carbonate. The resulting solution is concentrated under reduced pressure in a reactor, at a jacket temperature of about 70° C., until the total dissolved solids concentration is at least 20 to 70 wt %, such as from 30 to 60 wt %, from 40 to 50 wt %, or from 45 to 50 wt %. After concentration, the mixture can be cooled to 10° C. to 15° C. during which ammonium sulfate crystallizes. The mixture is further cooled to 4° C. to 10° C. and stirred for at least 30 minutes. The mixture is then filtered or centrifuged to remove ammonium sulfate crystals and aqueous filtrate 1 is isolated. The ammonium sulfate cake is washed with methanol and the methanol wash liquid is reserved. Filtration can be carried out using a Nutsche type filter or any suitable filter as determined by one skilled in the art of filtration of organic materials. Aqueous filtrate 1 is charged to a reactor and agitation is started. Optionally, crystals of ammonium sulfate isolated previously are added to the mixture to act as seed crystals. Methanol is added to the reactor and then the mixture is cooled to 10° C. to 15° C. The methanol wash liquid reserved in the previous step is added as a portion of the first methanol charge. A second portion of methanol is added to the reactor and the mixture is cooled to 4° C. to 10° C. The mixture is stirred at this temperature for at least 30 minutes. The mixture is filtered or centrifuged to remove ammonium sulfate crystals. The resultant aqueous filtrate 2 is isolated. The ammonium sulfate cake is washed with methanol and the wash filtrate is combined with the aqueous filtrate 2 to yield a "glufosinate solution." The "glufosinate solution" may be dried using a stream of air or gas at ambient pressure or under reduced pressure at ambient or elevated temperatures to yield the "L-glufosinate starting material."

II. METHODS FOR PREPARATION OF CRYSTALLINE L-GLUFOSINATE AMMONIUM MONOHYDRATE

Provided herein are methods for preparing crystalline L-glufosinate ammonium monohydrate. The crystalline L-glufosinate ammonium monohydrate contains L-glufosinate ammonium monohydrate Form B.

Method IIa: Final isolation. In one aspect, the final isolation method can include the following steps:
(i) forming a mixture comprising a glufosinate starting material, such as an "L-glufosinate starting material" optionally obtained from the desalting method described above, and an aqueous solution,
  wherein the glufosinate starting material comprises L-glufosinate ammonium and D-glufosinate ammonium, and
  wherein the aqueous solution comprises water and a water-miscible organic solvent;
(ii) crystallizing L-glufosinate ammonium monohydrate from the mixture of step (i) to form L-glufosinate ammonium monohydrate crystals; and,
(iii) separating at least a portion of the L-glufosinate ammonium monohydrate crystals from the aqueous solution following step (ii);
thereby preparing the crystalline L-glufosinate ammonium monohydrate. In some embodiments, L-glufosinate seed crystals are used in step (ii).

Method IIb: Final isolation. In another aspect, the method for preparing crystalline L-glufosinate can include the following steps:
(i) forming a mixture comprising a glufosinate starting material and an aqueous solution,
  wherein the glufosinate starting material comprises L-glufosinate ammonium and D-glufosinate ammonium, and
  wherein the aqueous solution comprises water, a water-miscible organic solvent and a source of ammonia;
(ii) crystallizing L-glufosinate ammonium monohydrate from the mixture of step (i) to form L-glufosinate ammonium monohydrate crystals; and
(iii) separating at least a portion of the L-glufosinate ammonium monohydrate crystals from the aqueous solution following step (ii); thereby preparing the crystalline L-glufosinate ammonium monohydrate.

The molar ratio of the L-glufosinate ammonium to the D-glufosinate ammonium in the glufosinate starting material and L-glufosinate starting material can vary, depending on factors such as the method by which the glufosinate was synthesized or the extent of purification conducted. The molar ratio L-glufosinate ammonium to D-glufosinate ammonium can range, for example, from about 50:50 to about 90:10, or from about 55:45 to about 85:15, or from about 60:40 to about 80:20, or from about 65:35 to about 75:25. In some embodiments, the molar ratio of the L-glufosinate ammonium to the D-glufosinate ammonium in the glufosinate starting material and L-glufosinate starting material is at least 50:50. In some embodiments, the molar ratio of the L-glufosinate ammonium to the D-glufosinate ammonium in the glufosinate starting material and L-glufosinate starting material is at least 70:30. In some embodiments, the molar ratio of the L-glufosinate ammonium to the D-glufosinate ammonium in the glufosinate starting material and L-glufosinate starting material is at least 76:24. In some embodiments, the molar ratio of the L-glufosinate ammonium to the D-glufosinate ammonium in the glufosinate starting material and L-glufosinate starting material is 50:50.

Other components, including impurities such as reaction byproducts, may also be present in the glufosinate starting material. In some embodiments, the glufosinate starting material and L-glufosinate starting material further comprise one or more components selected from the group consisting of L-glutamate and salts thereof, D-glutamate and salts thereof, L-pyroglutamate and salts thereof, 2-oxoglutarate and salts thereof, succinic acid and salts thereof, 2-oxo-4-(hydroxy(methyl)-phosphinoyl)butyric acid and salts thereof, sodium sulfate, ammonium sulfate, sodium chloride, ammonium chloride, sodium citrate, ammonium citrate, sodium carbonate, ammonium carbonate, sodium bicarbonate, ammonium bicarbonate, sodium formate, ammonium formate, sodium acetate, ammonium acetate, monosodium phosphate, disodium phosphate, monoammonium phosphate, and diammonium phosphate. In some embodiments, the glufosinate starting material comprises L-glutamate.

While the number and quantity of non-glufosinate components may vary, the amount of glufosinate in the glufosinate starting material and L-glufosinate starting material will be at least about 50% (w/w). The amount of glufosinate in the glufosinate starting material and L-glufosinate starting material may be, for example, at least 55% (w/w), or at least about 60% (w/w), or at least about 65% (w/w), or at least about 70% (w/w). The amount of glufosinate in the glufosinate starting material and L-glufosinate starting material may range from about 50% (w/w) to about 95% (w/w), or from about 55% (w/w) to about 90% (w/w), or from about 60% (w/w) to about 90% (w/w), or from about 65% (w/w) to about 90% (w/w), or from about 70% (w/w) to about 90% (w/w), or from about 75% (w/w) to about 90% (w/w). In some embodiments, the amount of glufosinate in the glufosinate starting material and L-glufosinate starting material ranges from about 70% (w/w) to about 90% (w/w). In some embodiments the amount of glufosinate in the glufosinate starting material and L-glufosinate starting material ranges from about 75% (w/w) to about 85% (w/w).

Aqueous solutions employed in the methods of the present disclosure generally contain water and a water-miscible organic solvent. By "miscible," it is meant that the organic solvent forms a homogeneous mixture with water, neither separating from the water nor reacting chemically with the water. Examples of water-miscible organic solvents include, but are not limited to, C1-6 alkanols, such as methanol, ethanol, n-propanol, isopropanol, n-butanol, sec-butanol, tert-butanol, n-pentanol, cyclopentanol, and cyclohexanol; low molecular weight amides such as N,N-dimethylformamide, N,N-dimethylacetamide, N-methyl-2-pyrrolidone, and the like; ketones and ketone-alcohols, such as acetone, methyl ethyl ketone, cyclohexanone and diacetone alcohol; water-miscible ethers, such as tetrahydrofuran, dioxane, and the like; and polyols such as ethylene glycol, diethylene glycol, triethylene glycol, polyethylene glycol, polypropylene glycol, and 1,2,6-hexanetriol; and sulfoxides, such as dimethyl sulfoxide and sulfolane.

In some embodiments, the water-miscible solvent is selected from the group consisting of methanol, ethanol, 1-propanol, 2-propanol, acetonitrile, tetrahydrofuran, 1,4-dioxane, 1-methyl-2-propanol, 1,2-propanediol, and 1,2-ethanediol. In some embodiments, the water-miscible organic solvent is methanol.

The ratio water-miscible organic solvent and water in the aqueous solution may vary, depending on factors such as the particular water-miscible organic solvent employed or the amount of glufosinate to be purified. Typically, the amount of the water-miscible organic solvent in the aqueous solution will be at least about 30% by volume. The ratio of water-miscible organic solvent to water in the aqueous solution may range, for example from about from about 30:70 to about 95:5, or from about 35:65 to about 95:5, or from about 40:60 to about 95:5, or from about 45:55 to about 95:5, or from about 50:50 to about 90:10, or from about 55:45 to about 85:15, or from about 60:40 to about 80:20, or from about 65:35 to about 75:25.

In some embodiments, the ratio of the water-miscible organic solvent to the water in the aqueous solution ranges from about 45:55 to about 95:5 to by volume. In some embodiments, the ratio of the water-miscible organic solvent to the water in the aqueous solution ranges from about 45:55 to about 65:35 to by volume. In some embodiments, the ratio of the water-miscible organic solvent to the water in the aqueous solution ranges from about 45:55 to about 55:45. In some embodiments, the ratio of the water-miscible organic solvent to the water in the aqueous solution is about 50:50. In some embodiments, the ratio of the water-miscible organic solvent to the water in the aqueous solution is about 60:40.

The aqueous solution employed in the methods generally contains an ammonia source such as gaseous ammonia or an ammonium salt such as ammonium hydroxide or ammonium carbonate, ranging in concentration from a few millimolar to one molar or higher. For example, the concentration of ammonium hydroxide in the aqueous solution may range from about 100 mM to about 750 mM, or from about 200 mM to about 600 mM, or from about 200 mM to about 550 mM, or from about 250 mM to about 500 mM, or from about 300 mM to about 450 mM, or from about 325 mM to about 425 mM, or from about 350 mM to about 400 mM, or from about 350 mM to about 370 mM. In some embodiments, the concentration of ammonium hydroxide in the aqueous solution ranges from about 0.1M to about 1M. In some embodiments, the concentration of ammonium hydroxide in the aqueous solution ranges from 350 mM to about 450 mM. In some embodiments, the aqueous solution does not contain ammonium hydroxide. In some embodiments, the isolated crystals can contain a mixture of Form A and Form B crystals.

The L-glufosinate starting material and the aqueous solution are combined in amounts such that the concentration of glufosinate in the resulting mixture is suitable for glufosinate crystal formation. Typically, the molar concentration of glufosinate in the L-glufosinate starting material, prior to crystallization, will be at least 100 mM (e.g., 250 mM or more, or 500 mM or more, or 1 M or more). In some embodiments, the ratio of the L-glufosinate starting material to the aqueous solution in step (i) (Method IIa and IIb) ranges from about 0.5:1 to about 5:1 by weight. In some embodiments, the ratio of the L-glufosinate starting material to the aqueous solution in step (i) (Method IIa and IIb) ranges from about 1:1 to about 2:1 by weight. The ratio of the L-glufosinate starting material to the aqueous solution in step (i) (Method IIa and IIb) may be, for example, about 1.1:1 by weight, or about 1.2:1 by weight, or about 1.3:1 by weight, or about 1.4:1 by weight, or about 1.5:1 by weight, or about 1.6:1 by weight, or about 1.7:1 by weight, or about 1.8:1 by weight, or about 1.9:1 by weight, or about 2:1 by weight.

Crystallizing L-glufosinate ammonium monohydrate may include heating the mixture containing the starting material and the aqueous solution. The mixture may be heated, for example, to a temperature ranging from about 40° C. to about 80° C., or higher, depending on factors such as the concentration of glufosinate in the mixture or the water-miscible organic solvent used in the aqueous solution. The mixture may be heated to a temperature of at least 40° C., or at least about 45° C., or at least about 50° C., or at least about 55° C., or at least about 60° C., or at least about 65° C., or at least about 70° C., or at least about 75° C., or at least about 80° C., or at least about 85° C., or at least about 90° C. In some embodiments, the mixture of step (i) (Method IIa and IIb) is heated to a temperature ranging from about 45° C. to about 55° C. and held at the raised temperature for a period of time ranging from about 5 minutes to about 24 hours. In some embodiments, the mixture of step (i) is heated to at least around 45° C. In some embodiments, the heated mixture is maintained at a temperature of at least 45° C. (e.g., at least 50° C., or at least 45° C.) for a period of time ranging from about 10 minutes to about 6 hours prior to separating L-glufosinate crystals from the mixture. In some embodiments, the heated mixture is maintained at about 45° C. or about 50° C. for at least about 1 hour. Following heating, the mixture may be cooled (e.g., to a temperature about 30° C. or less, such as about 25° C., or about 20° C., or about 4° C.).

Seed crystals containing glufosinate can be added to a heated or non-heated mixture containing the starting material and the aqueous solution, so as to promote formation of L-glufosinate ammonium monohydrate crystals. Typically, the molar ratio of L-glufosinate to D-glufosinate (L:D ratio) in the seed crystals will be at least around 90:10. In some embodiments, the glufosinate seed crystals comprise L-glufosinate ammonium monohydrate Form B. As described below, it has been discovered that an L:D ratio around 76:24 is a eutectic point above which L-glufosinate ammonium monohydrate can be efficiently crystallized from aqueous mixtures. Accordingly, seed crystals containing L-glufosinate can be added in an amount such that the L:D ratio for the total amount of glufosinate in the system is at least 76:24.

Mixtures containing glufosinate seed crystals are generally maintained at a temperature for a period of time sufficient for forming L-glufosinate ammonium monohydrate crystals, e.g., at 25-50° C. for periods of time ranging from a few minutes to a few days. In some embodiments, a mixture comprising the glufosinate seed crystals is maintained at a temperature around 30° C. for a period of time ranging from about 1 hour to about 24 hours prior to separating L-glufosinate ammonium monohydrate crystals from the mixture.

Glufosinate seed crystals can be added in an amount ranging, for example, from about 0.05% (w/w) to about 0.1% (w/w), or from about 0.1% (w/w) to about 0.5% (w/w), or from about 0.5% (w/w) to about 1% (w/w), or from about 1% (w/w) to about 5% (w/w), or from about 5% (w/w) to about 10% (w/w), or from about 10% (w/w) to about 20% (w/w), or from about 20% (w/w) to about 30% (w/w). In some embodiments, the glufosinate seed crystals are added in an amount ranging from about 0.05% (w/w) to about 30% (w/w) based on the amount of glufosinate in the L-glufosinate starting material. In some embodiments, the glufosinate seed crystals are added in an amount ranging from about 0.1% (w/w) to about 2.5% (w/w) based on the amount of glufosinate in the L-glufosinate starting material. In some embodiments, the glufosinate seed crystals are added in an amount ranging from about 0.1% (w/w) to about 0.5% (w/w) based on the amount of glufosinate in the L-glufosinate starting material.

L-glufosinate ammonium monohydrate crystals can be conveniently separated from aqueous mixtures by filtration, centrifugation, or a combination thereof. In some embodiments, crystals are isolated as a filter cake or centrifugation pellet which can then be washed with water, a water-miscible solvent, or a combination thereof. Isolated crystals can be dried under reduced pressure or at ambient pressure with air or a gas stream (e.g., nitrogen or argon), at ambient temperature or elevated temperature. For example, the crystals can be dried at a temperature from about 18 to 25° C., or from about 25 to 40° C. or from about 40 to 60° C. or from about 60 to 70° C. or from about 70 to 80° C. or from about 80 to 90° C. or from about 90 to 100° C. In some embodiments, the crystals are dried at 37° C. Drying can be monitored and stopped, for example, when the mass of a crystal sample no longer decreases due to water or solvent evaporation. Large agglomerates of crystals may be milled to reduce lumping of crystals. Accordingly, some embodiments of the disclosure provide methods as described above, wherein separating at least a portion of the L-glufosinate ammonium monohydrate crystals in step (iii) comprises filtering the mixture of step (ii), centrifuging the mixture of step (ii), or a combination thereof.

The size range of crystalline L-glufosinate ammonium monohydrate particles obtained by using the methods provided herein is convenient for use in formulations. In some embodiments, the crystals are mixed with water and other formulation ingredients to form an herbicidal product. In some embodiments, 90% of the crystalline L-glufosinate ammonium particles are less than about 350 microns as determined by volumetric distribution measurement basis (i.e., "$D_v90$"). For example, the $D_v90$ of the particles can be less than about 350 microns or less than about 300 microns or less than about 250 microns or less than about 200 microns or less than about 150 microns or less than about 125 microns or less than about 100 microns or less than about 75 microns or less than about 50 microns or less than about 25 microns.

Advantageously, crystalline L-glufosinate ammonium monohydrate prepared according to the methods provided herein is characterized by a high L:D ratio. While the crystalline product may contain some D-glufosinate, the L:D ratio of the crystalline product is significantly higher than the L:D ratio of the glufosinate starting material. In some embodiments, the molar ratio of L-glufosinate to D-glufosinate in the crystalline L-glufosinate ammonium monohydrate product is at least 90:10. The molar ratio of L-glufosinate to D-glufosinate in the crystalline L-glufosinate ammonium monohydrate product may be, for example, at least 91:9, or at least 92:8, or at least 93:7, or at least 94:6, or at least 95:5, or at least 96:4, or at least 97:3, or at least 98:2, or at least 99:1.

Crystalline product can be identified as L-glufosinate ammonium monohydrate Form B based on an X-ray powder diffraction (XRPD) pattern exhibiting at least three peaks (e.g., 3, 4, 5, 6, 7, 8, 9, 10, 11, 12, 13, 14, 15, 16, 17, 18, 19, 20, 21, 22, 23, 24, or 25 peaks) selected from 10.0, 11.4, 12.5, 16.5, 17.4, 18.1, 19.6, 20.0, 21.8, 22.9, 23.6, 24.0, 25.1, 25.5, 26.1, 26.3, 26.4, 27.9, 28.2, 28.4, 28.7, 29.2, 30.2, 30.9, 31.6, 31.7, 32.7, 33.0, 33.3, 34.3, 35.2, 36.7, 37.2, 37.4, 37.8, 38.3, 38.7, and 39.3°2θ, ±0.2°2θ, as determined on a diffractometer using Cu-Kα radiation. In some embodiments, the XRPD pattern comprises at least six peaks selected from 10.0, 12.5, 16.5, 17.4, 18.1, 19.6, 20.0, 21.8, 22.9, 23.6, 24.0, 25.5, 26.3, 26.4, 29.2, 34.3, 35.2, and 37.4°2θ, ±0.2°2θ. In some embodiments, the XRPD pattern comprises at least ten peaks selected from 10.0, 12.5, 16.5, 17.4, 18.1, 19.6, 20.0, 21.8, 22.9, 23.6, 24.0, 25.5, 26.3, 26.4, 29.2, 34.3, 35.2, and 37.4°2θ, ±0.2°2θ. In some embodiments, the XRPD pattern is substantially in accordance with FIG. 1.

Figure 2:
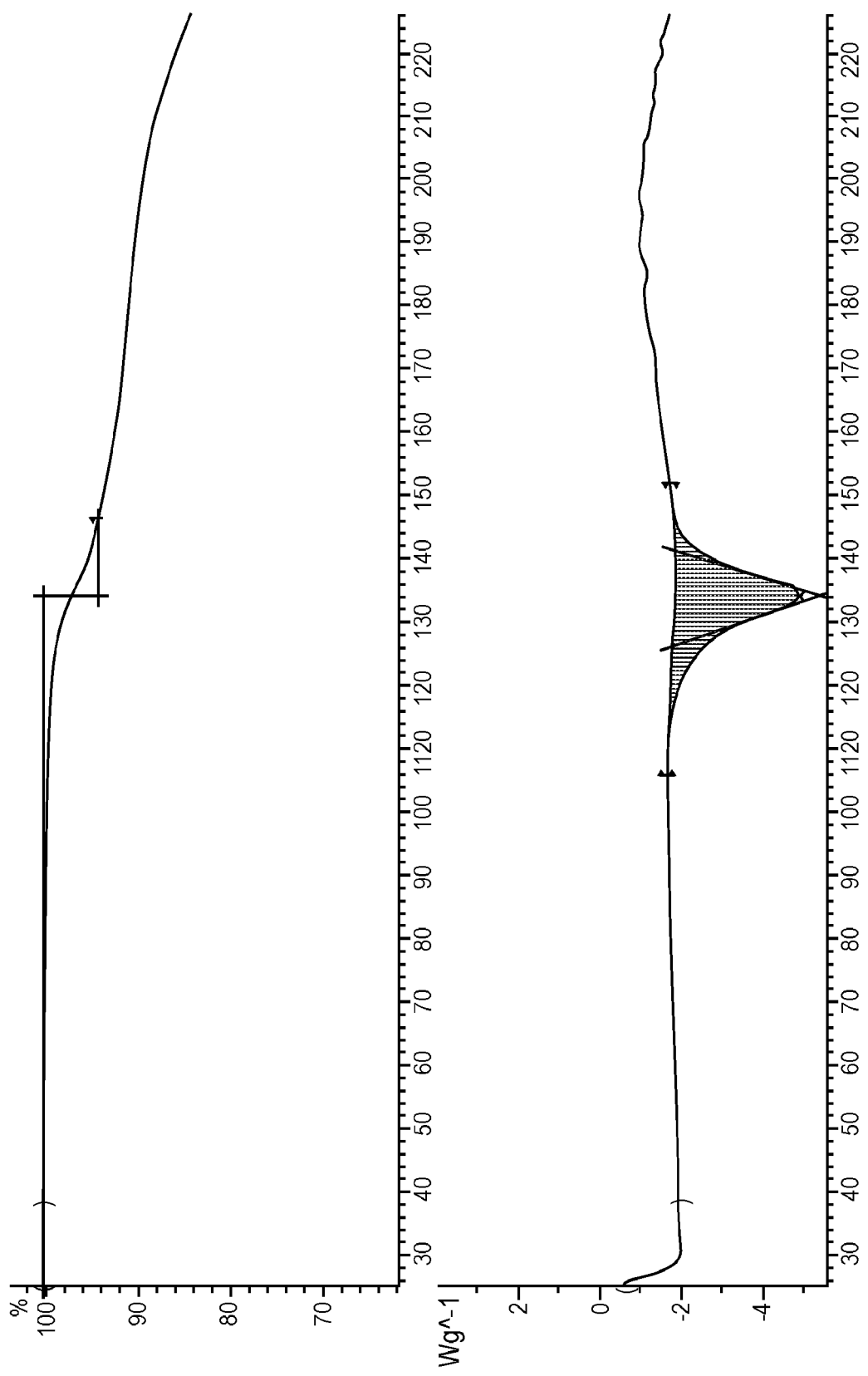
FIG. 2 shows thermogravimetric analysis (TGA) data for L-glufosinate ammonium monohydrate Form B, exhibiting a characteristic endotherm with onset at 123.4° C.
Figure 3:
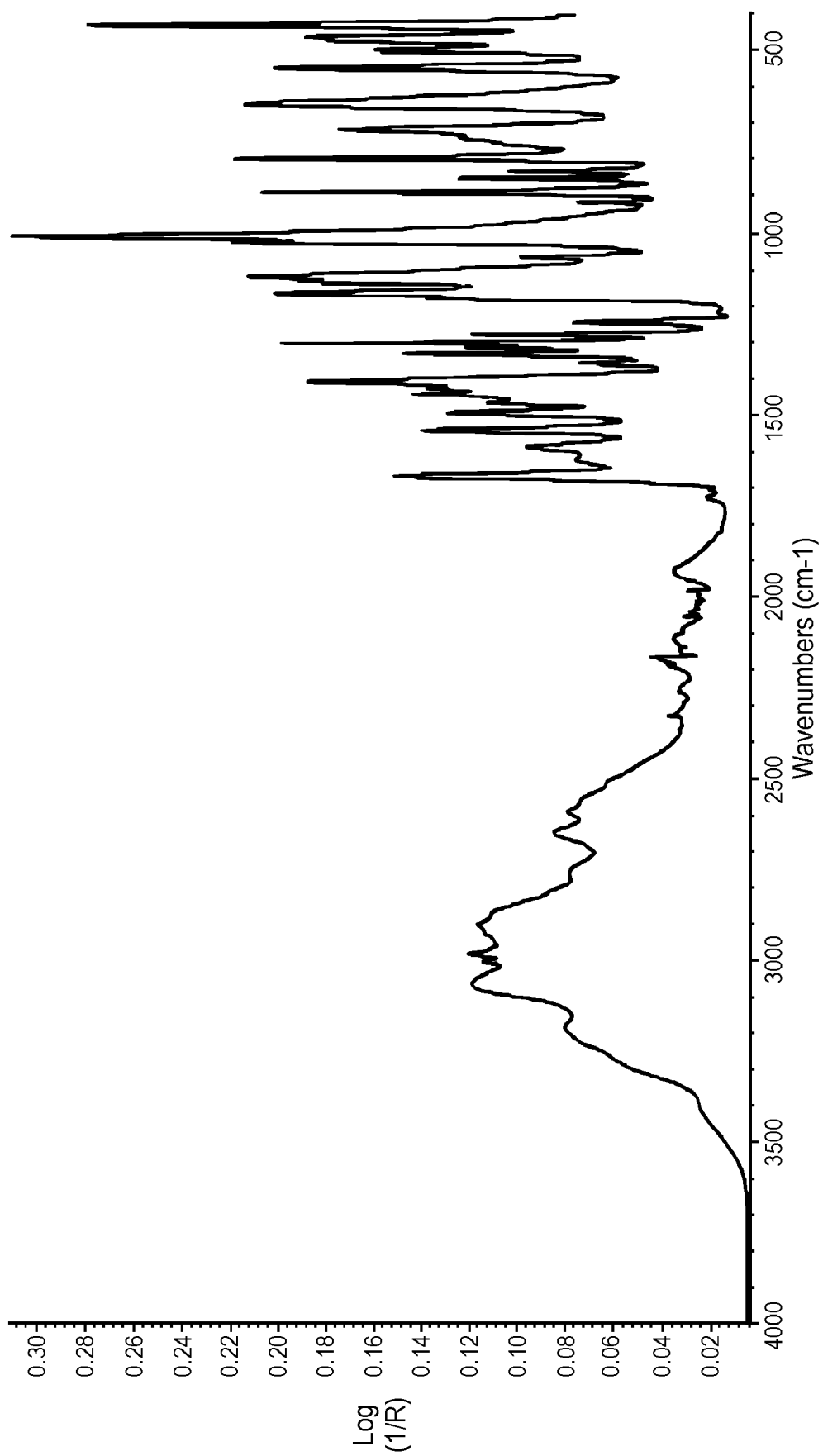
FIG. 3 shows infrared (IR) spectroscopy data for L-glufosinate ammonium monohydrate Form B.

In some embodiments, the L-glufosinate ammonium monohydrate Form B is characterized by a differential scanning calorimetry (DSC) curve exhibiting an endotherm with an onset around 123° C. In some embodiments, the L-glufosinate ammonium monohydrate Form B is characterized by a DSC curve substantially in accordance with FIG. 2. In some embodiments, the L-glufosinate ammonium monohydrate Form B is characterized by an IR spectrum substantially in accordance with FIG. 3.

A non-limiting example process according to the present disclosure can be conducted as follows. Solid L-glufosinate ammonium starting material, containing at ratio of at least 76.5% L-glufosinate ammonium to 23.5% D-glufosinate ammonium, and having total glufosinate ammonium composition of approximately 75% by weight is charged to a suitable container. To the container is added a mixture of methanol and water containing dilute ammonium hydroxide; the ratio of methanol to water can range from 70:30 to 50:50.

The mixture is heated to about 50° C. with stirring to ensure dissolution of the solids; additional means may be employed to assist with dissolution such as sonication, for example. After the mixture is aged for one hour, seed crystals of L-glufosinate ammonium hydrate ("Form B") are added to the mixture. The mixture is then slowly cooled to 30° C. in a stepwise fashion and mixed for about 16 hours. The resulting slurry is discharged from the container and centrifuged in portions. The resulting cake is washed with methanol; resuspension of the cake in methanol can also be included. After the second centrifugation, the solids are allowed to dry under ambient conditions.

III. COMPOSITIONS CONTAINING L-GLUFOSINATE MONOHYDRATE

Crystalline L-glufosinate ammonium monohydrate described herein can be used in compositions useful for application to a field of crop plants for the prevention or control of weeds. The composition may be formulated as a liquid for spraying on a field. The L-glufosinate is provided in the composition in effective amounts. For example, the amount of L-glufosinate ammonium monohydrate in the composition can be about 10 grams, about 50 grams, about 100 grams, about 150 grams, about 200 grams, about 250 grams, about 300 grams, about 350 grams, about 400 grams, about 450 grams, about 500 grams, about 550 grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250 grams, about 1,300 grams, about 1,350 grams, about 1,400 grams, about 1,450 grams, or about 1,500 grams L-glufosinate per hectare.

The herbicidal compositions (including concentrates which require dilution prior to application to the plants) described herein contain L-glufosinate ammonium monohydrate (i.e., the active ingredient), and one or more adjuvant components in liquid or solid form. In some instances, the herbicidal compositions also include residual D-glufosinate and/or PPO.

The compositions are prepared by admixing the active ingredient with one or more adjuvants, such as diluents, extenders, carriers, surfactants, organic solvents, humectants, or conditioning agents, to provide a composition in the form of a finely-divided particulate solid, pellet, solution, dispersion, or emulsion. Thus, the active ingredient can be used with an adjuvant, such as a finely-divided solid, a liquid of organic origin, water, a wetting agent, a dispersing agent, an emulsifying agent, or any suitable combination of these. In some embodiments, the L-glufosinate ammonium monohydrate is present in an amount ranging from about 10% (w/w) to 30% (w/w), based on the total weight of the formulated composition. From the viewpoint of economy and convenience, water is the preferred diluent. However, not all the compounds are resistant to hydrolysis and in some cases this may dictate the use of non-aqueous solvent media, as understood by those of skill in the art.

In some examples, the formulated composition can include one or more surfactants. A suitable surfactant for use in the formulated composition includes sodium alkyl ether sulfate. The surfactant can be present in an amount from 10% (w/w) to 40% (w/w) by weight of the formulated composition. The formulated composition can optionally include one or more organic solvents. Optionally, the solvent can be 1-methoxy-2-propanol, dipropylene glycol, ethylene glycol, and mixtures thereof. The one or more solvents can be present in an amount ranging from 0.5% (w/w) to 20% (w/w) by weight of the formulated composition.

The formulated composition can also include one or more polysaccharide humectants. Examples of suitable polysaccharide humectants include, for example, alkyl polysaccharides, pentoses, high fructose corn syrup, sorbitol, and molasses. The polysaccharide humectant, such as alkyl polysaccharide, can be present in the formulated composition in an amount ranging from 4% (w/w) to 20% (w/w) by weight of the formulated composition. A diluent can also be included in the formulated composition. Suitable diluents include water and other aqueous components. Optionally, the diluents are present in an amount necessary to produce compositions ready for packaging or for use.

The formulated compositions described herein, particularly liquids and soluble powders, can contain as further adjuvant components one or more surface-active agents in amounts sufficient to render a given composition readily dispersible in water or in oil. The incorporation of a surface-active agent into the compositions greatly enhances their efficacy. Surface-active agents, as used herein, include wetting agents, dispersing agents, suspending agents, and emulsifying agents. Anionic, cationic, and non-ionic agents can be used with equal facility. Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol), and polyoxyethylene derivatives of the mono-higher fatty acid esters of hexitol anhydrides (e.g., sorbitan). Exemplary dispersants include methyl cellulose, polyvinyl alcohol, sodium lignin sulfonates, polymeric alkyl naphthalene sulfonates, sodium naphthalene sulfonate, polymethylene bisnaphthalenesulfonate, and sodium N-methyl-N-(long chain acid) laurates.

Water-dispersible powder compositions can be made containing one or more active ingredients, an inert solid extender, and one or more wetting and dispersing agents. The inert solid extenders are usually of mineral origin, such as the natural clays, diatomaceous earth, and synthetic minerals derived from silica and the like. Examples of such extenders include kaolinites, attapulgite clay, and synthetic magnesium silicate. Aqueous suspensions can be prepared by dissolution or by mixing together and grinding an aqueous slurry of a water-insoluble active ingredient in the presence of a dispersing agent to obtain a concentrated slurry of very finely-divided particles. The resulting concentrated aqueous suspension is characterized by its extremely small particle size, so that when diluted and sprayed, coverage is very uniform. Emulsifiable oils are usually solutions of active ingredients in water-immiscible or partially water-immiscible solvents together with a surface-active agent. Suitable solvents for the active ingredient described herein include hydrocarbons and water-immiscible ethers, esters, or ketones. Further components suitable for use in the formulated compositions provided herein are described in WO 2019/018406 and U.S. Pat. Nos. 4,692,181 and 5,258,358, which are incorporated herein by reference in their entirety.

The formulated compositions described herein can also contain other additives, for example, fertilizers, phytotoxicants and plant growth regulators, pesticides, and the like used as adjuvants or in combination with any of the above-described adjuvants. The formulated compositions described herein can also be admixed with the other materials, e.g., fertilizers, other phytotoxicants, etc., and applied in a single application.

It is recognized that the formulated herbicidal compositions can be used in combination with other herbicides. The herbicidal compositions described herein are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the formulated herbicidal compositions described herein include: amide herbicides such as allidochlor, 6-arylpicolinates, beflubutamid, benzadox, benzipram, bromobutide, cafenstrole, CDEA, chlorthiamid, 6-cyclopropylpicolinates, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; pyrimidinedione herbicides such as saflufenacil; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen,nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, 2-Methyl-4-chlorophenoxyacetic acid (MCPA), MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orb encarb, pebulate, prosulfocarb, pyributicarb, sulfallate, thiobencarb, tiocarbazil, tri-allate and vemolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, aminocyclopyrachlor, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compositions of the present invention can, further, be used in conjunction with glyphosate, dicamba, or 2,4-D on glyphosate-tolerant, dicamba-tolerant, or 2,4-D-tolerant crops. It is generally preferred to use the compositions described herein in combination with herbicides that are selective for the crop being treated and which complement the spectrum of weeds controlled by these compositions at the application rate employed. It is further generally preferred to apply the compositions described herein and other complementary herbicides at the same time, either as a combination formulation or as a tank mix.

IV. METHODS OF USING

The compositions described herein can be used in methods for selectively controlling weeds in an agricultural field or any other area, including, for example, a railway, lawn, golf course, and others where the control of weeds is desired. Optionally, the field or other area can contain a crop of planted seeds or crops that are resistant to glufosinate. The methods can include applying an effective amount of a composition comprising L-glufosinate as described herein to the field.

The compositions described herein are useful for application to a field of crop plants for the prevention or control of weeds. The compositions may be formulated as a liquid for spraying on a field. The L-glufosinate is provided in the compositions in effective amounts. As used herein, effective amount means from about 10 grams active ingredient per hectare to about 1,500 grams active ingredient per hectare, e.g., from about 50 grams to about 400 grams or from about 100 grams to about 350 grams. In some embodiments, the active ingredient is L-glufosinate. For example, the amount of L-glufosinate in the composition can be about 10 grams, about 50 grams, about 100 grams, about 150 grams, about 200 grams, about 250 grams, about 300 grams, about 350 grams, about 400 grams, about 500 grams, about 550 grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250 grams, about 1,300 grams, about 1,350 grams, about 1,400 grams, about 1,450 grams, or about 1,500 grams L-glufosinate per hectare.

V. EXEMPLARY EMBODIMENTS

1. A method for preparing crystalline L-glufosinate ammonium monohydrate, the method comprising
 (i) forming a mixture comprising a L-glufosinate starting material and an aqueous solution, wherein:
 the L-glufosinate starting material comprises L-glufosinate ammonium and D-glufosinate ammonium, and
 the aqueous solution comprises water and a water-miscible organic solvent;
 (ii) crystallizing L-glufosinate ammonium monohydrate from the mixture of step (i) to form L-glufosinate ammonium monohydrate crystals; and
 (iii) separating at least a portion of the L-glufosinate ammonium monohydrate crystals from the aqueous solution following step (ii);
 thereby preparing the crystalline L-glufosinate ammonium monohydrate,
 wherein the crystalline L-glufosinate ammonium monohydrate comprises L-glufosinate ammonium monohydrate Form B.

2. The method of embodiment 1, wherein the aqueous solution further comprises an ammonia source.

3. The method of embodiment 2, wherein the ammonia source is ammonium hydroxide.

4. The method of any one of embodiments 1-3, wherein the molar ratio of the L-glufosinate ammonium to the D-glufosinate ammonium in the glufosinate starting material is at least 70:30.

5. The method of any one of embodiments 1-4, wherein the molar ratio of the L-glufosinate ammonium to the D-glufosinate ammonium in the glufosinate starting material is at least 50:50.

6. The method of any one of embodiments 1-4, wherein the molar ratio of the L-glufosinate ammonium to the D-glufosinate ammonium in the glufosinate starting material is at least 76:24.

7. The method of any one of embodiments 1-6, wherein the L-glufosinate starting material further comprises one or more components selected from the group consisting of L-glutamate and salts thereof, D-glutamate and salts thereof, L-pyroglutamate and salts thereof, 2-oxoglutarate and salts thereof, succinic acid and salts thereof, 2-oxo-4-(hydroxy (methyl)phosphinoyl)butyric acid and salts thereof, sodium sulfate, ammonium sulfate, sodium chloride, ammonium chloride, monosodium phosphate, disodium phosphate, monoammonium phosphate, and diammonium phosphate.

8. The method of embodiment 7, wherein the L-glufosinate starting material comprises L-glutamate.

9. The method of any one of embodiments 1-8, wherein the amount of glufosinate in the L-glufosinate starting material ranges from about 70% (w/w) to about 90% (w/w).

10. The method of embodiment 9, wherein the amount of glufosinate in the L-glufosinate starting material ranges from about 75% (w/w) to about 85% (w/w).

11. The method of any one of embodiments 1-10, wherein the water-miscible solvent is selected from the group consisting of methanol, ethanol, 1-propanol, 2-propanol, acetonitrile, tetrahydrofuran, 1,4-dioxane, 1-methyl-2-propanol, 1,2-propanediol, and 1,2-ethanediol.

12. The method of embodiment 11, wherein the water-miscible organic solvent is methanol.

13. The method of any one of embodiments 1-12, wherein the ratio of the water-miscible organic solvent to the water in the aqueous solution ranges from about 45:55 to about 95:5 to by volume.

14. The method of any one of embodiments 1-13, wherein the ratio of the water-miscible organic solvent to the water in the aqueous solution ranges from about 45:55 to about 65:35 to by volume.

15. The method of any one of embodiments 1-14, wherein the concentration of ammonium hydroxide in the aqueous solution ranges from about 0.1M to about 1M.

16. The method of embodiment 15, wherein the concentration of ammonium hydroxide in the aqueous solution is about 0.4 M.

17. The method of any one of embodiments 1-16, wherein the ratio of the L-glufosinate starting material to the aqueous solution in step (i) ranges from about 0.5:1 to about 5:1 by weight.

18. The method of embodiment 17, wherein the ratio of the L-glufosinate starting material to the aqueous solution in step (i) ranges from about 1:1 to about 2:1 by weight.

19. The method of any one of embodiments 1-18, wherein step (ii) comprises heating the mixture of step (i) to form a heated mixture.

20. The method of embodiment 19, wherein the mixture of step (i) is heated to at least around 45° C.

21. The method of embodiment 19 or embodiment 20, wherein the heated mixture is maintained at a temperature of at least around 45° C. for a period of time ranging from about 10 minutes to about 6 hours prior to step (iii).

22. The method of any one of embodiments 19-21, further comprising cooling the heated mixture to form a cooled mixture prior to step (iii).

23. The method of embodiment 22, wherein the heated mixture is cooled to a temperature around 30° C. or less.

24. The method of any one of embodiments 1-18, wherein step (ii) comprises adding glufosinate seed crystals to the mixture of step (i).

25. The method of any one of embodiments 19-23, comprising adding glufosinate seed crystals to the heated mixture of step (ii).

26. The method of embodiment 24 or embodiment 25, wherein the glufosinate seed crystals comprise L-glufosinate ammonium monohydrate Form B.

27. The method of any one of embodiments 24-26, wherein the mixture comprising the glufosinate seed crystals is maintained at a temperature around 30° C. for a period of time ranging from about 1 hour to about 24 hours prior to step (iii).

28. The method of any one of embodiments 24-27, wherein the glufosinate seed crystals are added in an amount ranging from about 0.05% (w/w) to about 30% (w/w) based on the amount of glufosinate in the L-glufosinate starting material.

29. The method of embodiment 28, wherein the glufosinate seed crystals are added in an amount ranging from about 0.1% (w/w) to about 0.5% (w/w) based on the amount of glufosinate in the L-glufosinate starting material.

30. The method of any one of embodiments 1-29, wherein separating at least a portion of the L-glufosinate crystals in step (iii) comprises filtering the mixture of step (ii), centrifuging the mixture of step (ii), or a combination thereof.

31. The method of any one of embodiments 1-30, further comprising one or more steps of (iv) washing the L-glufosinate ammonium monohydrate crystals; and (v) drying the L-glufosinate ammonium monohydrate crystals.

32. The method of any one of embodiments 1-31, wherein the crystalline L-glufosinate ammonium monohydrate further comprises D-glufosinate.

33. The method of embodiment 32, wherein the molar ratio of L-glufosinate to D-glufosinate is at least 90:10.

34. The method of embodiment 32 or embodiment 33, wherein the molar ratio of L-glufosinate to D-glufosinate is at least 95:5.

35. The method of any one of embodiments 1-34, wherein the L-glufosinate ammonium monohydrate Form B is characterized by an X-ray powder diffraction (XRPD) pattern comprises at least three peaks selected from 10.0, 11.4, 12.5, 16.5, 17.4, 18.1, 19.6, 20.0, 21.8, 22.9, 23.6, 24.0, 25.1, 25.5, 26.1, 26.3, 26.4, 27.9, 28.2, 28.4, 28.7, 29.2, 30.2, 30.9, 31.6, 31.7, 32.7, 33.0, 33.3, 34.3, 35.2, 36.7, 37.2, 37.4, 37.8, 38.3, 38.7, and 39.3°2θ, ±0.2°2θ, as determined on a diffractometer using Cu-Kα radiation.

36. The method of any one of embodiments 1-35, wherein the L-glufosinate ammonium monohydrate Form B is characterized by a differential scanning calorimetry (DSC) curve exhibiting an endotherm with an onset around 123° C.

37. Crystalline L-glufosinate ammonium monohydrate prepared according to the method of any one of embodiments 1-36, wherein the crystalline L-glufosinate ammonium monohydrate comprises L-glufosinate ammonium monohydrate Form B.

38. Crystalline L-glufosinate ammonium monohydrate according to embodiment 37, further comprising D-glufosinate.

39. Crystalline L-glufosinate ammonium monohydrate according to embodiment 38, wherein the molar ratio of L-glufosinate to D-glufosinate is at least 90:10.

40. Crystalline L-glufosinate ammonium monohydrate according to embodiment 38 or embodiment 39, wherein the molar ratio of L-glufosinate to D-glufosinate is at least 95:5.

41. A method of preparing crystalline L-glufosinate from a glufosinate mixture, comprising:
(i) preparation of immobilized enzymes wherein said enzymes are D-amino acid oxidase (DAAO) enzymes and transaminase enzymes;
(ii) contacting said glufosinate mixture to the immobilized enzymes to obtain an L-glufosinate rich composition;
(iii) conducting chromatographic purification of the composition of step (ii) to isolate L-glufosinate;

42. A method of preparing crystalline L-glufosinate from a composition comprising both D-glufosinate and L-glufosinate, said method comprising:
(i) Contacting said composition with a DAAO and a transaminase enzyme;
(ii) Allowing enzymatic reactions to occur to obtain a composition of greater than 70% L-glufosinate;
(iii) crystallization of L-glutamic acid from the composition of step (ii);
(iv) chromatographic purification to obtain a composition comprising L-glufosinate;
(v) Desalting of the composition of step (iv); and (vi) Isolating L-glufosinate from the composition of step (v) by crystallization.

43. A method of separating salts from glufosinate starting material, comprising:
(i) dissolving the glufosinate starting material in an aqueous solution;
(ii) adjusting the pH of solution to be between 6 and 7;
(iii) concentrating the solution until the total dissolved solids concentration is at least 20 to 70 wt % (e.g., 30 to 60 wt %, 40 to 50 wt %, or 45 to 50 wt %);
(iv) cooling the concentrated solution to 2 to 15° C.;
(v) separating the crystallized salt using filtration or centrifugation; and
(vi) drying the remaining solution to isolate glufosinate ammonium monohydrate.

44. A method of embodiment 43, wherein the salt is selected from a group consisting of ammonium sulfate, sodium sulfate, ammonium citrate, sodium citrate, ammonium carbonate, sodium carbonate, ammonium formate, sodium formate, ammonium acetate, sodium acetate, ammonium bicarbonate and sodium bicarbonate.

45. A method of embodiment 44 wherein the salt is ammonium sulfate.

46. The method of any one of embodiments 42-45 wherein said DAAO enzyme comprises the amino acid sequence set forth in SEQ ID NO: 2.

47. The method of any one of embodiments 42-45 wherein said DAAO enzyme comprises the amino acid sequence set forth in SEQ ID NO: 3.

48. A mutant DAAO enzyme wherein said enzyme comprises the amino acid sequence set forth in SEQ ID NO: 2.

49. A mutant DAAO enzyme wherein said enzyme comprises the amino acid sequence set forth in SEQ ID NO: 3.

50. A mutant DAAO enzyme wherein said enzyme comprises the amino acid sequence set forth in SEQ ID NO: 5.

The following examples are offered by way of illustration and not by way of limitation.

VI. EXAMPLES

Example 1. Characterization of Crystalline L-Glufosinate Ammonium Monohydrate Form B Single crystal X-ray diffraction analysis provided the crystal form and unit structure of L-glufosinate ammonium monohydrate Form B as referenced in Table 1:

TABLE 1

| Crystal system, space group | Monoclinic, P2$_1$ |
| --- | --- |
| Data collectiontemperature (K) | 150 |
| a (Å) | 8.1752 (3) |
| b (Å) | 6.7270 (3) |
| c (Å) | 9.3283 (4) |
| β (°) | 108.7776 (9) |
| Volume (Å$^3$) | 485.70 (4) |
| Z | 2 |

Analysis of crystalline material by X-Ray Powder Diffraction (XRPD) has assigned the pattern in FIG. 1 (top trace) to L-glufosinate ammonium monohydrate. This pattern matches "Form B" in FIG. 1 (bottom trace) crystallized and isolated in previous studies. Assay of ammonium content by ion chromatography and water content by Karl Fisher analysis content show that crystals consistent with XRPD pattern of "Form B" contain stochiometric amounts of water and ammonia (Table 2).

Characterization of crystals (AG-990-6-26) by HPLC showed that the amount of glufosinate free acid was 76.29% (w/w). Glutamate was the major impurity at 0.47% (w/w). 2-Oxoglutarate and L-pyroglutamate were present at <0.1% (w/w). Water, 7.50% (w/w); ammonia, 6.79% (w/w); sodium, 3.55% (w/w); and sulfate, 5.09% (w/w) constituted the remaining mass in the crystalline material.

TABLE 2

Mass balance of L-glufosinate ammonium hydrate Form B crystals

| Analyte | Method | Result (wt %) |
| --- | --- | --- |
| Water | Karl Fisher Titration | 7.50 |
| 2-oxoglutarate | HPLC | 0.08 |
| Glutamic acid | HPLC | 0.47 |
| L-pyroglutamic acid | HPLC | 0.07 |
| Glufosinate (free acid) | HPLC | 76.29 |
| Ammonia | Ion Chromatography | 6.97 |
| Sodium | ICP | 3.55 |
| Sulfate | Ion Chromatography | 5.09 |
| Methanol | Gas Chromatography | <0.01 |
| Total | | 100.02 |

Example 2. Characterization of Crystalline L-Glufosinate Ammonium Monohydrate Form A Single crystal X-ray diffraction analysis provided the crystal form and unit structure of L-glufosinate ammonium monohydrate Form A as referenced in Table 3:

TABLE 3

Single crystal X-ray diffraction analysis of Form A

| Crystal system, space group | Monoclinic, P2$_1$ |
| --- | --- |
| Data collection temperature (K) | 149 |
| a (Å) | 8.4962(5) |
| b (Å) | 6.6124(3) |
| c (Å) | 9.1042(5) |
| β (°) | 106.525(2) |
| Volume (Å$^3$) | 490.35(5) |
| Z | 2 |

Figure 4:
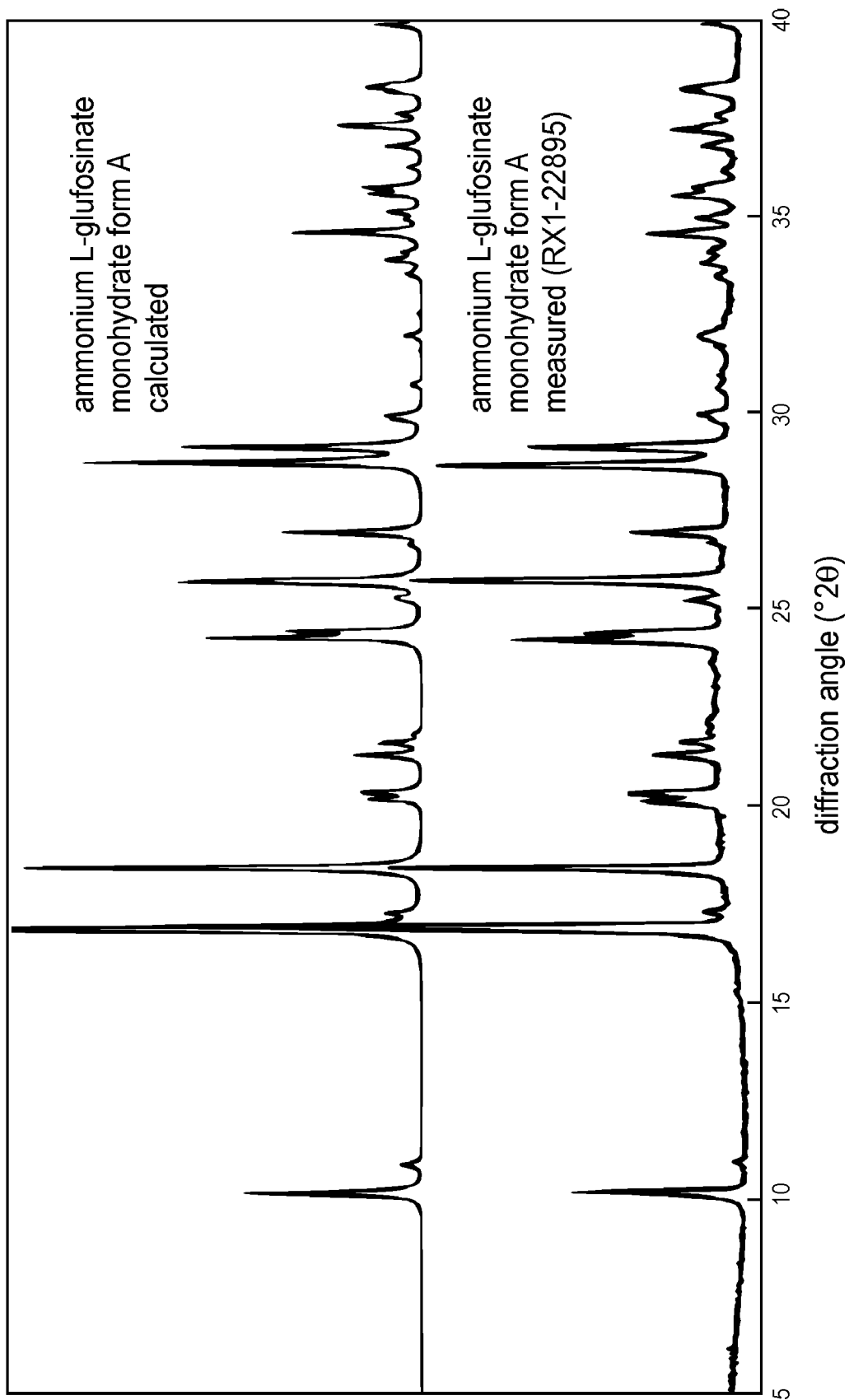
FIG. 4 shows X-ray powder diffraction (XRPD) data for L-glufosinate ammonium monohydrate Form A.

Analysis of crystalline material by X-Ray Powder Diffraction (XRPD) has assigned the pattern in FIG. 4 (top trace) to L-glufosinate ammonium monohydrate. This pattern matches "Form A" in FIG. 4 (bottom trace) crystallized and isolated in previous studies.

Example 3. Antisolvent:Solvent Ratio Studies

Antisolvent:solvent ratio studies were conducted with material containing 76.4% (w/w) total glufosinate ammonium and having an L-glufosinate:D-glufosinate (L:D) ratio of 81:19. Fluid mixtures containing methanol, water, and ~0.4 M ammonium hydroxide were employed as shown in Table 4.

TABLE 4

Antisolvent:solvent ratio studies

| Sample No. | MeOH:Water Ratio | Weight % of Starting Material in the batch | L:D ratio of Crystals | Weight % L-glufosinate ammonium hydrate in crystals |
| --- | --- | --- | --- | --- |
| 2-1 | 50:50 | 65.0% | 100.0% | 93.7% |
| 2-2 | 60:40 | 64.2% | 100.0% | 93.5% |

TABLE 4-continued

Antisolvent:solvent ratio studies

| Sample No. | MeOH: Water Ratio | Weight % of Starting Material in the batch | L:D ratio of Crystals | Weight % L-glufosinate ammonium hydrate in crystals |
|---|---|---|---|---|
| 2-3 | 70:30 | 62.4% | 99.3% | 94.7% |
| 2-4 | 80:20 | 55.3% | 87.5% | 72.3% |
| 2-5 | 90:10 | 50.0% | 83.7% | 71.9% |

Crystals with enriched L:D-glufosinate ratios were obtained from a single direct crystallization in all solvent systems. L:D-glufosinate ratios of >99:1 were obtained in solvent systems of 50:50 to 70:30 methanol:water. Purity of crystals as L-glufosinate ammonium hydrate in >90% was also obtained in solvent systems of 50:50 to 70:30 methanol:water.

Example 4. Determination of Eutectic

Investigation of crystallization of L-glufosinate ammonium lots with total glufosinate ammonium purities of 75-80% and L:D-glufosinate ratios of 72:28 to 81:19 was conducted at 30° C. for 16 hours as shown in Tables 5 and 6. The ratio of methanol to water for these experiments was 50:50 (v:v). Samples were taken after six hours of mixing at room temperature (Table 5) and again after 12 days of mixing at room temperature (Table 6). Lots 17, 18, 19, 20 and 21 resulted in L-glufosinate ammonium hydrate crystals after the six-hour mixing period that were substantially enriched in L-glufosinate (Table 5). Crystals were not observed in Lots 13 and 15 after the six-hour period, but longer mixing time did result in crystal formation in these lots (Table 6). However, Lots 13 and 15 contained an initial ratio of 72:28 and 76:24 L-glufosinate to D-glufosinate, respectively, and the crystals obtained from these two lots were not enriched in the L-glufosinate isomer (Table 6). The other lots processed with the procedure afforded crystals with L:D ratios substantially greater than 50:50 (Table 6). Comparing the results from Lots 16 and 20 indicates a eutectic point around an L:D-glufosinate ratio of about 76:24.

TABLE 5

Lots processed after 16 hours crystallization at 30° C. and 6 hours at room temperature

| Lot No. | Initial L:D ratio | Sample | Weight % L-glufosinate ammonium | Weight % L-glufosinate ammonium hydrate in crystals | L:D Ratio | Recovery of L-glufosinate ammonium from starting material |
|---|---|---|---|---|---|---|
| 13 | 72:28 | Isolated crystals | — | No visible crystals | — | — |
|  |  | Mother liquor | — | — | — | — |
| 15 | 77.9:22.1 | Isolated crystals | — | No visible crystals | — | — |
|  |  | Mother liquor | — | — | — | — |
| 16 | 76:24 | Isolated crystals | — | 57.1% | 55.4:44.6 | 15.3% |
|  |  | Mother liquor | 35.6% | — | 81.5:18.5 | — |
| 17 | 77.7:22.3 | Isolated crystals | — | 55.7% | 74.1:15.9 | 15.2% |
|  |  | Mother liquor | 37.0% | — | 80.5:19.5 | — |
| 18 | 78.5:21.5 | Isolated crystals | — | 9.8% | 83.2:16.8 | 3.61% |
|  |  | Mother liquor | 34.5% | — | 79.8:20.2 | — |
| 19 | 81:19 | Isolated crystals | — | 90.8% | 97.4:2.6 | 37.3% |
|  |  | Mother liquor | 27.4% | — | 84.6:15.4 | — |
| 20 | 76.5:23.5 | Isolated crystals | — | 55.2% | 91.7:8.3 | 7.02% |
|  |  | Mother liquor | 34.5% | — | 80.8:19.2 | — |
| 21 | 81:19 | Isolated crystals | — | 84.3% | 95.0:5.0 | 47.6% |
|  |  | Mother liquor | 34.9% | — | 83.5:16.5 | — |

TABLE 6

Lots processed after 16 hour crystallization at 30° C. and 12 days at room temperature.

| Lot No. | Initial L:D ratio | Sample description | Weight % L-glufosinate ammonium | Weight % L-glufosinate ammonium hydrate in crystals | Final L:D Ratio | Recovery of L-glufosinate ammonium from starting material |
|---|---|---|---|---|---|---|
| 13 | 72:28 | Isolated crystals | — | 51.0% | 54.0:46.0 | 11.5% |
|  |  | Mother liquor | 35.3% | — | 66.5:33.5 | — |
| 15 | 77.9:22.1 | Isolated crystals | — | 92.3% | 98.7:1.3 | 9.40% |
|  |  | Mother liquor | 36.9% | — | 64.6:35.4 | — |
| 16 | 76:24 | Isolated crystals | — | 61.1% | 62.9:37.1 | 20.8% |
|  |  | Mother liquor | 37.9% | — | 66.3:33.7 | — |
| 17 | 77.7:22.3 | Isolated crystals | — | 84.8% | 88.4:11.6 | 61.6% |
|  |  | Mother liquor | 26.4% | — | 47.8:52.2 | — |
| 18 | 78.5:21.5 | Isolated crystals | — | 24.7% | 97.2:2.8 | 8.20% |
|  |  | Mother liquor | 34.6% | — | 66.6:33.4 | — |

TABLE 6-continued

Lots processed after 16 hour crystallization at 30° C. and 12 days at room temperature.

| Lot No. | Initial L:D ratio | Sample description | Weight % L-glufosinate ammonium | Weight % L-glufosinate ammonium hydrate in crystals | Final L:D Ratio | Recovery of L-glufosinate ammonium from starting material |
|---|---|---|---|---|---|---|
| 19 | 81:19 | Isolated crystals | — | 89.8% | 98.5:1.5 | 54.5% |
|  |  | Mother liquor | 17.6% | — | 61.1:38.9 | — |
| 20 | 76.5:23.5 | Isolated crystals | — | 92.8% | 98.7:1.3 | 63.0% |
|  |  | Mother liquor | 12.2% | — | 53.3:46.7 | — |
| 21 | 81:19 | Isolated crystals | — | 92.5% | 100:0 | 62.0% |
|  |  | Mother liquor | 13.1% | — | 57.3:42.7 | — |

Example 5. Twenty Gram-Scale Crystallization Process

L-Glufosinate ammonium starting material (20 g; 76.4% total glufosinate ammonium, L:D-glufosinate ammonium ratio 81:19) was added to 12.5 mL of 50:50 (v:v) water:methanol solution with 0.36 M ammonium hydroxide at room temperature with stirring. The temperature was raised to 45° C. with sonication to dissolve solids, then the solution was placed into a shaker at 30° C. After 1 hr, L-glufosinate ammonium monohydrate seed crystals (>70% wt L-glufosinate ammonium purity, L:D-glufosinate ratio >97:3) as 0.2% wt of the starting material (g/g) were added. The slurry was stirred for 16 hours at 30° C. for crystallization. The precipitated crystals were centrifuged, washed with methanol, filtered, and dried to yield 7.8 g of purified L-glufosinate ammonium monohydrate crystals: L-glufosinate ammonium monohydrate purity 89.8% wt; L:D-glufosinate ratio 98.5:1.5; recovery of 54.5% of L-glufosinate ammonium from the starting material.

Example 6. One Hundred Gram-Scale Crystallization Process

L-Glufosinate ammonium starting material (100 g; 76.4% total glufosinate ammonium, L:D-glufosinate ammonium ratio 81:19) was added to 62 mL of 40:60 (v:v) water:methanol solution with 0.36 M ammonium hydroxide at room temperature with stirring. The temperature was raised to 50° C. with stirring to dissolve solids, then the solution was held at 50° C. for 1 hr before addition of 100 mg of L-glufosinate ammonium monohydrate seed crystals (>70% wt L-glufosinate purity, >97:3 L:D-glufosinate ratio) in slurry with 10 mL methanol. After seeding, solution was held at 50° C. for 20 minutes, then temperature was cooled to 45° C. and held for 1 hr. After 1 hr, the temperature was lowered to 40° C. with a 1 hr hold before lowering it to 30° C. for overnight crystallization. The slurry was stirred for 16 hours at 30° C. for crystallization. After 30 minutes at room temperature, the precipitated crystals were centrifuged, washed with methanol, filtered, and dried to yield 53.2 g of purified L-glufosinate ammonium monohydrate crystals: L-glufosinate ammonium monohydrate purity 86.5% wt; L:D-glufosinate ratio 96.2:3.8; recovery of 68.6% of L-glufosinate ammonium from the starting material.

Example 7. Two Kilogram-Scale Crystallization Process

L-Glufosinate ammonium starting material (2000 g; 76.4% total glufosinate ammonium, L:D-glufosinate ammonium ratio 81:19) was added to 1140 g of 48:52 methanol:water (0.4 M NH$_4$OH) at room temperature with stirring. The slurry was transferred to a 5 L jacketed crystallization vessel. The temperature was raised to 50° C. to dissolve solids (stirring at 400 rpm), then held at 50° C. for 1 hr before addition of 40 g of L-glufosinate ammonium seed crystals (>70% wt L-glufosinate ammonium purity, L:D-glufosinate ratio >97:3) as 2% wt of the starting material (g/g) were added as slurry in 40 mL of methanol. The stirring was reduced to 250 rpm after addition of seed crystals. After 30 minutes, the temperature was reduced to 45° C. The batch temperature was reduced by 5° C. after each 30-minute temperature hold until temperature was 35° C. After 30 minutes at 35° C., stirring was reduced to 200 rpm and temperature was allowed to cool to room temperature for overnight crystallization (14-18 hours). The precipitated crystals were centrifuged, washed with methanol, filtered, and dried to yield 1071 g of purified L-glufosinate ammonium monohydrate crystals: L-glufosinate ammonium monohydrate purity 84.1% wt; L:D-glufosinate ratio 96.4:3.6; recovery of 65.8% of L-glufosinate ammonium from the starting material.

Example 8. Recrystallization Process

L-Glufosinate ammonium starting material (82.4 g; 76.4% total glufosinate ammonium, L:D-glufosinate ammonium ratio 97.8:2.2) was added to 35.4 g of 70:30 (v:v) water:methanol solution at room temperature with stirring. The temperature was raised to 60° C. with stirring to dissolve solids. After approximately 1 hr of heating at 60° C., 160 mL of methanol was added with stirring to crash out inorganic salt. The resulting slurry was centrifuged to pellet inorganic salt as a solid precipitant, and the mother liquor was decanted and allowed to crystallize over 16 hrs at room temperature. Crystals were filtered, washed with methanol, and dried to yield 46.5 g of purified L-glufosinate ammonium monohydrate crystals: L-glufosinate ammonium monohydrate purity 99.2% wt; L:D-glufosinate ratio 99.2:0.8; recovery of 68.6% of L-glufosinate ammonium from the starting material.

Example 9: Crystallization of L-Glufosinate Ammonium Monohydrate with the Addition of an Ammonia Source L-glufosinate ammonium starting material (50 g, 77% total L-glufosinate ammonium, 7.3% ammonium glutamate) was added to 36.7 g of 45:55 (w:w) methanol:water solution with an overall concentration of 0.4 M ammonium hydroxide at room temperature with stirring. The temperature was raised to 50° C. with sonication to dissolve solids. The solution was transferred into a glass roundbottom flask with overhead stirring and mixed at 250 RPM for one hour with the temperature maintained at 50° C. throughout. One gram of L-glufosinate ammonium monohydrate Form B seed crystals (>90% wt L-glufosinate ammonium purity) was added to the batch as a slurry in 3 mL of methanol. After 30 minutes the temperature was reduced to 45° C. The batch temperature was further reduced by 5° C. after each 30-minute hold period until the temperature was 30° C. Three milliliters of methanol were added and the slurry was stirred for 16 hours at 30° C. After 30 minutes at room temperature the slurry was diluted with 25 mL of methanol and filtered. Crystals were washed with methanol and dried to yield 20.7 g of L-glufosinate ammonium monohydrate crystals (L-glufosinate ammonium monohydrate purity 93.3%, recovery 45.5% from starting material, <1% D-glufosinate ammonium, and 0.58% ammonium glutamate). The crystals were analyzed by X-ray powder diffraction and the resulting pattern was consistent with that of L-glufosinate ammonium monohydrate Form B. The solids were measured for particle size and the $D_v 90$ was found to be 70.7 microns.

Example 10: Crystallization of L-Glufosinate Ammonium Monohydrate without the Addition of an Ammonia Source L-glufosinate ammonium starting material (50 g, 77% total L-glufosinate ammonium, 7.3% ammonium glutamate) was added to 35.0 g of 45:55 (w:w) methanol:water. No ammonium hydroxide was added. The temperature was raised to 50° C. with sonication to dissolve solids. The solution was transferred into a glass roundbottom flask with overhead stirring and mixed at 250 RPM for one hour with the temperature maintained at 50° C. throughout. One gram of L-glufosinate ammonium monohydrate Form B seed crystals (>90% wt L-glufosinate ammonium purity) was added to the batch as a slurry in 3 mL of methanol. After 30 minutes the temperature was reduced to 45° C. The batch temperature was further reduced by 5° C. after each 30-minute hold period until the temperature was 30° C. Three milliliters of methanol were added and the slurry was stirred for 16 hours at 30° C. After 30 minutes at room temperature the slurry was diluted with 25 mL of methanol and filtered. Crystals were washed with methanol and dried to yield 12.5 g of L-glufosinate ammonium monohydrate crystals (L-glufosinate ammonium monohydrate purity 97.0%, recovery 28.7% from starting material, <1% D-glufosinate ammonium and 0.69% ammonium glutamate). The crystals were analyzed by X-ray powder diffraction and the resulting pattern was consistent with that of L-glufosinate ammonium monohydrate Form B, however several peaks consistent with L-glufosinate ammonium monohydrate Form A were present. The solids were measured for particle size and the $D_v 90$ was found to be 102 microns.

Example 11: Crystallization of L-Glufosinate Ammonium Monohydrate with the Addition of Racemic Glufosinate L-glufosinate ammonium starting material (37.5 g, 72.4% total L-glufosinate ammonium, 11.4% glutamate ammonium) and racemic glufosinate ammonium (12.5 g, 95% total glufosinate ammonium), were added to 30.5 g of 50:50 (w:w) methanol:water solution with an overall concentration of 0.4M ammonium hydroxide at room temperature with stirring. The temperature was raised to 50° C. with sonication to dissolve solids. The solution was placed into a glass roundbottom flask with overhead stirring and mixed at 250 RPM for one hour with the temperature maintained at 50° C. throughout. One gram of L-glufosinate ammonium monohydrate Form B seed crystals (>90% wt L-glufosinate ammonium purity) was added as a slurry in 3 mL of methanol. After 30 minutes the temperature was reduced to 45° C. The batch temperature was further reduced by 5° C. after each 30-minute hold period until temperature was 30° C. Three milliliters of methanol were added and slurry was stirred for 16 hours at 30° C. After 30 minutes at room temperature the slurry was diluted with 25 mL of methanol and filtered. The crystals were washed with methanol and dried to yield 20.6 g of L-glufosinate ammonium monohydrate crystals (L-glufosinate ammonium monohydrate purity 94.4%, recovery 51.8% from starting material, containing <1% D-glufosinate ammonium and 0.7% D-glufosinate ammonium monohydrate, 1.53% ammonium glutamate).

Example 12: Preparation of Crystalline L-Glufosinate

Crystallization of L-Glutamic Acid

A solution containing L-glufosinate and L-glutamic acid, prepared as described in Example 1 of WO 2019/018406, is charged to a reactor and agitation is started. Concentrated sulfuric acid is charged to the reactor until the batch reaches pH 5.0 to 6.0; the batch is cooled as necessary to keep the temperature between 20 and 40° C. during the sulfuric acid addition. After complete addition of sulfuric acid, seed crystals of L-glutamic acid are added to the batch to facilitate crystal growth. With seed crystals mixing in the batch, concentrated sulfuric acid is added to the batch until the batch reaches pH 3.5 to 3.9 and then the batch is cooled to 0-5° C. and held at this temperature for at least 15 minutes. After the hold period, the batch is filtered to remove the L-glutamic acid crystals. The filtrate is concentrated under vacuum with a maximum jacket temperature of 70° C. until the total dissolved solids is greater than or equal to 28 wt %.

Chromatography

The concentrated filtrate is fed to a chromatography system followed by water eluent. Chromatography can be operated either in batch mode or in simulated moving bed (SMB) mode. Chromatography columns are packed with a hydroxylated polyacrylate or hydroxylated polymethacrylate resin. Separation occurs as the pulse of feed travels through the resin and partially purified L-glufosinate ammonium is collected from the front edge of the pulse downstream of the feed location. Water feed continues after the product has been collected to prepare the resin for subsequent feeding of concentrated filtrate.

Desalting

The fractions containing partially purified L-glufosinate solution is charged to a reactor and agitation is started. The pH of the solution is adjusted to between pH 6 and 7 using ammonium hydroxide. The batch is concentrated under vacuum until the total dissolved solids concentration is at least 48 to 50 wt %. The maximum jacket temperature for the concentration step is 70° C. After concentration, the batch is cooled to 10 to 15° C. during which ammonium sulfate crystallizes. The batch is mixed at 4 to 10° C. for at least 30 minutes and then filtered to remove ammonium sulfate crystals. The ammonium sulfate cake is washed with methanol, but the methanol wash is not immediately combined with the filtrate.

The aqueous filtrate is charged to a reactor and agitation is started. Optionally, crystals of ammonium sulfate isolated previously can be added to the batch to act as seed crystals. A portion of methanol is added to the reactor and then the batch is cooled to 10 to 15° C. The methanol cake wash is added as a portion of the first methanol charge. A second portion of methanol is added to the reactor. The batch is stirred at 4 to 10° C. for at least 30 minutes and then the batch is filtered to remove ammonium sulfate crystals. The ammonium sulfate cake is washed with methanol and the wash filtrate is combined with the batch.

Preparation of Starting Material for Crystallization

The filtrate, which has been desalted, is charged to a reactor and concentrated under vacuum until the concentration of total dissolved solids is approximately 48 wt %. The maximum jacket temperature during the concentration step is 70° C. The concentrated solution is transferred to a vacuum dryer where the batch is concentrated under vacuum to produce a solid with less than 5% total moisture.

Crystallization

The solid material is charged to a reactor and combined with methanol and aqueous ammonium hydroxide. The slurry is heated with mixing to 50 to 55° C. and held until the solids have dissolved. A slurry consisting of L-glufosinate ammonium monohydrate Form B seed crystals and methanol is charged to the reactor. After 30 minutes of mixing, the batch temperature is reduced from 50° C. to 45° C. The temperature is lowered in 5° C. increments followed by 30 minutes of mixing time until the batch temperature reaches 30° C. A small charge of methanol is added and then the batch is mixed at 30° C. for at least 12 hours. After the mixing time, the batch is cooled to 20 to 25° C. and methanol is added to the batch. After 30 minutes of mixing, the batch is filtered. The filter cake is washed with methanol and the resulting filter cake is dried under heat and vacuum to obtain L-glufosinate ammonium monohydrate Form B crystals.

Example 13: Improved and Variant DAAO Enzymes for Carrying Out Enzymatic Reactions DAAO Sequences The coding sequence of a mutant DAAO from *Rhodosporidium toruloides* (for example, consisting of a MGSSHHHHHHSSGLVPRGSHMMARIRL (SEQ ID NO: 4) leader sequence and the F58K and M213S mutations) was cloned into the pET14b vector to allow for expression of an N terminally 6xHis tagged protein. This pET14b-RgDAAO plasmid was transformed into BL21 (BE3) trxB pLysS cells. The sequence of the wild type DAAO from *Rhodosporidium toruloides* to which the numbering described for the first four entries in Table 7 corresponds (Ac302, Mut5, Mut7 (SEQ ID NO: 3), and Mut18), is shown in SEQ ID NO: 1. The sequence of the fifth entry in Table 7, Mut846, is provided in SEQ ID NO: 2. SEQ ID NO: 5 represents the Mut7 sequence with the linker SEQ ID NO: 4.

Stock Solutions:

The following dye stock solutions were prepared: a 20 mg/mL stock solution of 2,4,6-tribromo-3-hydroxybenzoic acid (TBHBA) in DMSO; and a 100 mg/mL stock solution of 4-aminoantipyrine (4-AAP) in water. The following enzyme stock solution was prepared: a 1 mg/mL stock solution of horseradish peroxidase (HRP) type 6 in a pH 8.0 potassium phosphate buffer. The following substrate stock solution was prepared: varying concentrations of racemic glufosinate in a pH 8.0 potassium phosphate buffer such that the initial reaction concentrations of racemic glufosinate were 0, 1, 10, 100, 250, and 500 nM. DAAO enzymes were made in *E. coli* which were lysed and the cell free extracts freeze dried. Enzyme amounts in the cell free extracts were quantified using SDS-PAGE and staining by Coomassie Blue.

Reaction Mixes:

The following reaction mixtures were prepared:

Mix A is a combination of the substrate and HRP enzyme. Solutions were prepared for each substrate concentration to be assayed using reaction buffer. The solutions were two times the final substrate concentration and 0.2 mg/mL for the HRP solution.

Mix B is a dye mixture. To 5 mL of reaction buffer was added 120 μL of TBHBA solution and 400 μL of 4-AAP solution.

Mix C is an enzyme mixture. A 0.02 mg/mL solution of DAAO in reaction buffer was prepared. The final DAAO concentration in the reaction was 5 μg/mL.

Protocol:

A spectrophotometer was used at a wavelength of 460 nm. The temperature for performing the assays was 30° C. The measurement was made at 15 minutes. Using a 96-well plate, the following mixes (with replicates) were added in the following order using multi-channel: 100 μl mix A, 50 μl mix B, and 50 μl mix C.

The enzyme kinetics were measured as described above, plotted on a Michaelis Menten graph, and used to calculate Vmax. As shown below in Table 7, variant mutant DAAO enzymes showed a range of activities:

TABLE 7

Variation of activity with enzyme sequence

| Variant | 54 | 56 | 58 | 213 | Vmax (umole/min/mg) |
|---|---|---|---|---|---|
| Ac302 | V | T | Q | S | 3.85 |
| Mut5 | V | T | H | S | 2.43 |
| Mut7 | V | N | H | S | 6.09 |
| Mut18 | L | N | H | S | 4.75 |
| Mut846 | n/a | n/a | n/a | n/a | 5.54 |

SEQUENCES

SEQ ID NO: 1:
MHSQKRVVVLGSGVIGLSSALILARKGYSVHILARDLPEDVSSQTFASPW
AGANWTPFMTLTDGPRQAKWEESTFKKWVELVPTGHAMWLKGTRRFAQNE
DGLLGHWYKDITPNYRPLPSSECPPGAIGVTYDTLSVHAPKYCQYLAREL
QKLGATFERRTVTSLEQAFDGADLVVNATGLGAKSIAGIDDQAAEPIRGQ
TVLVKSPCKRCTMDSSDPASPAYIIPRPGGEVICGGTYGVGDWDLSVNPE
TVQRILKHCLRLDPTISSDGTIEGIEVLRHNVGLRPARRGGPRVEAERIV
LPLDRTKSPLSLGRGSARAAKEKEVTLVHAYGFSSAGYQQSWGAAEDVAQ
LVDEAFQRYHGAARESKL

SEQ ID NO: 2:
MASPSNKQIVVLGAGVIGLTTAVKIQEQRGYQVTIIAEILPSDPKSIRYT
SHWAGAHHVSLAGEDKLQARVDQETFGVMWEMSAPGGEAEGCFLRQKQVE
YYCDKQADPHPLEHMPDFRRLDENSLIPNTVAGIGFTTLTIDTPIYLNYL
LSRFLARGGAIVRGSVQHISQVVDGGARVFTGSKSAGVPVDAVIVCAGIG
ARFLGGVEDKDVYPIRGQTVLLRAPWIRFGRTMSSKDGLYTYIIPRRSGD
VIVGGIKVPNDWYPTPRPETTQDILKRGLALCPELAPQSIRDQREPTVDD
LRPLVIEEGCGLRPGRKGGIRLEVEWYAKTDGQAPKVPIVHNYGHGGAGF
QASWGSASVALELLEKALAQARLAM

SEQ ID NO: 3:
MHSQKRVVVLGSGVIGLSSALILARKGYSVHILARDLPEDVSSQTFASPW
AGAVWNPHMTLTDGPRQAKWEESTFKKWVELVPTGHAMWLKGTRRFAQNE
DGLLGHWYKDITPNYRPLPSSECPPGAIGVTYDTLSVHAPKYCQYLAREL
QKLGATFERRTVTSLEQAFDGADLVVNATGLGAKSIAGIDDQAAEPIRGQ
TVLVKSPCKRCTSDSSDPASPAYIIPRPGGEVICGGTYGVGDWDLSVNPE
TVQRILKHCLRLDPTISSDGTIEGIEVLRHNVGLRPARRGGPRVEAERIV
LPLDRTKSPLSLGRGSARAAKEKEVTLVHAYGFSSAGYQQSWGAAEDVAQ
LVDEAFQRYHGAARESKL

-continued

SEQUENCES

SEQ ID NO: 4:
MGSSHEIHHHHSSGLVPRGSHMMARIRL

SEQ ID NO: 5:
MGSSHEIHHEIHSSGLVPRGSHMMARIRLMHSQKRVVVLGSGVIGLSSAL
ILARKGYSVHILARDLPEDVSSQTFASPWAGAVWNPHMTLTDGPRQAKWE
ESTFKKWVELVPTGHAMWLKGTRRFAQNEDGLLGHWYKDITPNYRPLPSS
ECPPGAIGVTYDTLSVHAPKYCQYLARELQKLGATFERRTVTSLEQAFDG
ADLVVNATGLGAKSIAGIDDQAAEPIRGQTVLVKSPCKRCTSDSSDPASP
AYIIPRPGGEVICGGTYGVGDWDLSVNPETVQRILKHCLRLDPTISSDGT
IEGIEVLRHNVGLRPARRGGPRVEAERIVLPLDRTKSPLSLGRGSARAAK
EKEVTLVHAYGFSSAGYQQSWGAAEDVAQLVDEAFQRYHGAARESKL

It is understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about" or the term "around". The term "about" and "around" are used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. If "X" were the value modified by "about" or "around," "about X" or "around X" would generally indicate a value from 0.95X to 1.05X including, for example, from 0.98X to 1.02X or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

What is claimed is:

1. A method for preparing crystalline L-glufosinate ammonium monohydrate, the method comprising:
   (i) forming a mixture comprising a L-glufosinate starting material and an aqueous solution,
   wherein the glufosinate starting material comprises L-glufosinate ammonium and D-glufosinate ammonium, and
   wherein the aqueous solution comprises water and a water-miscible organic solvent;
   (ii) crystallizing L-glufosinate ammonium from the mixture of step (i) to form L-glufosinate ammonium monohydrate crystals; and
   (iii) separating at least a portion of the L-glufosinate ammonium monohydrate crystals from the aqueous solution following step (ii);
   thereby preparing the crystalline L-glufosinate ammonium monohydrate,
   wherein the crystalline L-glufosinate ammonium monohydrate comprises L-glufosinate ammonium monohydrate Form B.

2. The method of claim 1, wherein the aqueous solution further comprises of an ammonia source.

3. The method of claim 2, wherein the ammonia source is ammonium hydroxide.

4. The method of claim 1, wherein the molar ratio of the L-glufosinate ammonium to the D-glufosinate ammonium in the glufosinate starting material is at least 70:30.

5. The method of claim 1, wherein the molar ratio of the L-glufosinate ammonium to the D-glufosinate ammonium in the L-glufosinate starting material is at least 76:24.

6. The method of claim 1, wherein the L-glufosinate starting material further comprises one or more components selected from the group consisting of L-glutamate and salts thereof, D-glutamate and salts thereof, L-pyroglutamate and salts thereof, 2-oxoglutarate and salts thereof, succinic acid and salts thereof, 2-oxo-4-(hydroxy(methyl)phosphinoyl) butyric acid and salts thereof, sodium sulfate, ammonium sulfate, sodium chloride, ammonium chloride, monosodium phosphate, disodium phosphate, monoammonium phosphate, and diammonium phosphate.

7. The method of claim 6, wherein the L-glufosinate starting material comprises L-glutamate.

8. The method of claim 1, wherein the amount of glufosinate in the L-glufosinate starting material ranges from about 70% (w/w) to about 90% (w/w).

9. The method of claim 8, wherein the amount of glufosinate in the L-glufosinate starting material ranges from about 75% (w/w) to about 85% (w/w).

10. The method of claim 1, wherein the water-miscible solvent is selected from the group consisting of methanol, ethanol, 1-propanol, 2-propanol, acetonitrile, tetrahydrofuran, 1,4-dioxane, 1-methyl-2-propanol, 1,2-propanediol, and 1,2-ethanediol.

11. The method of claim 10, wherein the water-miscible organic solvent is methanol.

12. The method of claim 1, wherein the ratio of the water-miscible organic solvent to the water in the aqueous solution ranges from about 45:55 to about 95:5 by volume.

13. The method of claim 1, wherein the ratio of the water-miscible organic solvent to the water in the aqueous solution ranges from about 45:55 to about 65:35 by volume.

14. The method of claim 1, wherein the concentration of ammonium hydroxide in the aqueous solution ranges from about 0.1M to about 1M.

15. The method of claim 14, wherein the concentration of ammonium hydroxide in the aqueous solution is about 0.4 M.

16. The method of claim 1, wherein the ratio of the L-glufosinate starting material to the aqueous solution in step (i) ranges from about 0.5:1 to about 5:1 by weight.

17. The method of claim 16, wherein the ratio of the L-glufosinate starting material to the aqueous solution in step (i) ranges from about 1:1 to about 2:1 by weight.

18. The method of claim 1, wherein step (ii) comprises heating the mixture of step (i) to form a heated mixture.

19. The method of claim 18, wherein the mixture of step (i) is heated to at least around 45° C.

20. The method of claim 17, wherein the heated mixture is maintained at a temperature of at least around 45° C. for a period of time ranging from about 10 minutes to about 6 hours prior to step (iii).

21. The method of claim 18, further comprising cooling the heated mixture to form a cooled mixture prior to step (iii).

22. The method of claim 21, wherein the heated mixture is cooled to a temperature around 30° C. or less.

23. The method of claim 1, wherein step (ii) comprises adding glufosinate seed crystals to the mixture of step (i).

24. The method of claim 18, comprising adding glufosinate seed crystals to the heated mixture of step (ii).

25. The method of claim 23, wherein the glufosinate seed crystals comprise L-glufosinate ammonium monohydrate Form B.

26. The method of claim 23, wherein the mixture comprising the glufosinate seed crystals is maintained at a temperature around 30° C. for a period of time ranging from about 1 hour to about 24 hours prior to step (iii).

27. The method of claim 23, wherein the glufosinate seed crystals are added in an amount ranging from about 0.05% (w/w) to about 30% (w/w) based on the amount of glufosinate in the L-glufosinate starting material.

28. The method of claim 27, wherein the glufosinate seed crystals are added in an amount ranging from about 0.1% (w/w) to about 0.5% (w/w) based on the amount of glufosinate in the L-glufosinate starting material.

29. The method of claim 1, wherein separating at least a portion of the L-glufosinate crystals in step (iii) comprises filtering the mixture of step (ii), centrifuging the mixture of step (ii), or a combination thereof.

30. The method of claim 1, further comprising one or more steps of (iv) washing the L-glufosinate ammonium monohydrate crystals; and (v) drying the L-glufosinate ammonium monohydrate crystals.

31. The method of claim 1, wherein the crystalline L-glufosinate ammonium monohydrate further comprises D-glufosinate.

32. The method of claim 31, wherein the molar ratio of L-glufosinate to D-glufosinate is at least 90:10.

33. The method of claim 31, wherein the molar ratio of L-glufosinate to D-glufosinate is at least 95:5.

34. The method of claim 1, wherein the L-glufosinate ammonium monohydrate Form B is characterized by an X-ray powder diffraction (XRPD) pattern comprises at least three peaks selected from 10.0, 11.4, 12.5, 16.5, 17.4, 18.1, 19.6, 20.0, 21.8, 22.9, 23.6, 24.0, 25.1, 25.5, 26.1, 26.3, 26.4, 27.9, 28.2, 28.4, 28.7, 29.2, 30.2, 30.9, 31.6, 31.7, 32.7, 33.0, 33.3, 34.3, 35.2, 36.7, 37.2, 37.4, 37.8, 38.3, 38.7, and 39.3°2θ, ±0.2°2θ, as determined on a diffractometer using Cu-Kα radiation.

35. The method of claim 1, wherein the L-glufosinate ammonium monohydrate Form B is characterized by a differential scanning calorimetry (DSC) curve exhibiting an endotherm with an onset around 123° C.

* * * * *